United States Patent [19]

Bundgaard et al.

[11] Patent Number: 4,742,073
[45] Date of Patent: May 3, 1988

[54] PILOCARPINE PRODRUGS

[76] Inventors: Hans Bundgaard, 36, Tjørnevej, DK-2970 Hørsholm; Erik Falch, 31, Olgasvej, DK-2950 Vedbæk; Claus S. Larsen, 15, Hulegaardsvej, DK-4320 Lejre, all of Denmark; Thomas J. Mikkelson, The University of Kansas, School of Pharmacy,, Lawrence, Kans. 66045

[21] Appl. No.: 533,646

[22] Filed: Sep. 16, 1983

[30] Foreign Application Priority Data

Sep. 17, 1982 [DK] Denmark ............................. 4170/82

[51] Int. Cl.$^4$ .......................................... C07D 263/04
[52] U.S. Cl. .................................. 514/400; 548/225; 548/235; 548/248; 548/243; 548/336; 548/342
[58] Field of Search ............................. 548/342, 336; 424/273 R; 514/397, 400, 333, 341; 546/256, 278

[56] References Cited

U.S. PATENT DOCUMENTS

| | | | |
|---|---|---|---|
| 3,470,197 | 9/1969 | Van Dyke, Jr. ...................... | 548/336 |
| 3,631,059 | 12/1971 | Goorley et al. ....................... | 548/336 |
| 4,045,558 | 8/1977 | Smith et al. ....................... | 548/336 X |
| 4,061,722 | 12/1977 | Bodor ............................. | 548/336 X |

FOREIGN PATENT DOCUMENTS 0106541  4/1984  European Pat. Off. ............. 548/342

OTHER PUBLICATIONS

Fox, Chem. Reviews, 32, (1943), pp. 59-62 and 68.
Hussain, et al., Journal of Pharmaceutical Sciences, vol. 65, (1976), pp. 1510-1512.
Mitra, et al.; Int. Jour. of Pharmaceutics, 10 (1982), pp. 219-229.
Koda, et al.; Jour. Pharm. Sci., 62, (1973), pp. 2021-2023.
Lee, et al.; Jour. Pharm. Sci., 68, (1979), pp. 673-684.
Lerman, et al.; Canad. J. Ophthal. 6, (1971), pp. 14-23.
Norell, et al.; Brit. Jour. of Opthalmology, 64, (1980), pp. 137-141.
Patton, et al.; Amer. Jour. of Opthalmology, 85, (1978), pp. 225-229.
Shell, et al., Annals of Ophthalmology, Oct. 1974, pp. 1037-1045.
Norell; Pharmacy International, April 1982, pp. 123-125.
Anderson, et al.; Invest. Opthalmol. Vis. Sci., 19 (1980), pp. 817-823.
Bundgaard, et al.; Int. Jour. of Pharmaceutics, 10 (1982), pp. 281-289.
Noller, The Chemistry of Organic Compounds, 3rd Ed. (1965), pp. 193.

*Primary Examiner*—Joseph P. Brust
*Attorney, Agent, or Firm*—Stiefel, Gross, Kurland & Pavane

[57] ABSTRACT

Compounds are disclosed of the general formula I

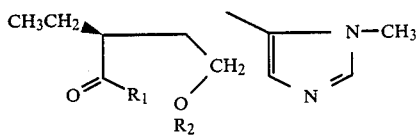

wherein $R_1$ is a group of the formula II $$R_3-X- \qquad II$$

wherein $R_3$ is alkyl; phenyl; phenyl substituted with halogen, lower alkyl, hydroxy, lower alkoxy, or phenoxy; phenyl-lower alkyl in which the phenyl group may be substituted with halogen, lower alkyl, hydroxy, lower alkoxy, or phenoxy; phenyl-lower alkenyl in which the phenyl group may be substituted with halogen, lower alkyl, hydroxy, lower alkoxy or phenoxy; and X is oxygen or sulfur; or $R_1$ is a group of the formula III (Abstract continued on next page.)

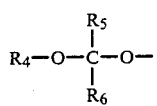   III wherein $R_4$ has the same meaning as $R_3$ as defined above; or $R_4$ is a group of the formula IV

   IV wherein $R_7$ has the same meaning as $R_3$ as defined above; or $R_7$ is an aromatic 5- or 6-membered heterocyclic ring containing one or two heteroatoms selected from the group consisting of nitrogen, oxygen, and sulfur; and wherein $R_5$ and $R_6$ are the same or different and each represent hydrogen or have the same meaning as $R_3$ as defined above;

or $R_1$ is a group of the formula V

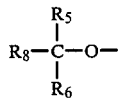   V wherein $R_5$ and $R_6$ are as defined above and $R_8$ is polyhalogenated lower alkyl or a group of the formula VI

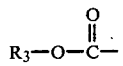   VI wherein $R_3$ is as defined above; or $R_1$ is a group of the formula VII

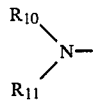   VII wherein $R_{10}$ and $R_{11}$ together with the adjacent nitrogen atom form a 5- or 6-membered heterocyclic ring, which in addition to the nitrogen may contain one or two further heteroatoms selected from the group consisting of nitrogen, oxygen, and sulfur;

or $R_1$ is a group of the formula VIII

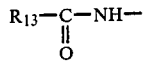   VIII wherein $R_{13}$ is a group of the formula II, wherein $R_3$ and X are as defined above; or $R_{13}$ is a group of the formula VIIa

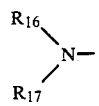   VIIa wherein $R_{16}$ and $R_{17}$ are the same or different and each represent hydrogen or have the same meaning as $R_3$ as defined above; or $R_{13}$ is a group of the formula VII, wherein $R_{10}$ and $R_{11}$ are as defined above;

or $R_1$ is a group of the formula IX

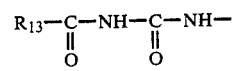   IX wherein $R_{13}$ is as defined above; and $R_2$ is hydrogen or a group of the formula IV, wherein $R_7$ is as defined above; or $R_2$ is a group of the formula VI, wherein $R_3$ is as defined above; and salts thereof.

The compounds of the formula I are prodrugs of pilocarpine. When administered ophthalmically to a warm-blooded animal, such as a human, compounds of formula I, due to their high lipophilicity, will penetrate the cornea in an extent greater than pilocarpine itself, and will thereafter be converted into pilocarpine in a slow and controlled manner.

14 Claims, 7 Drawing Sheets

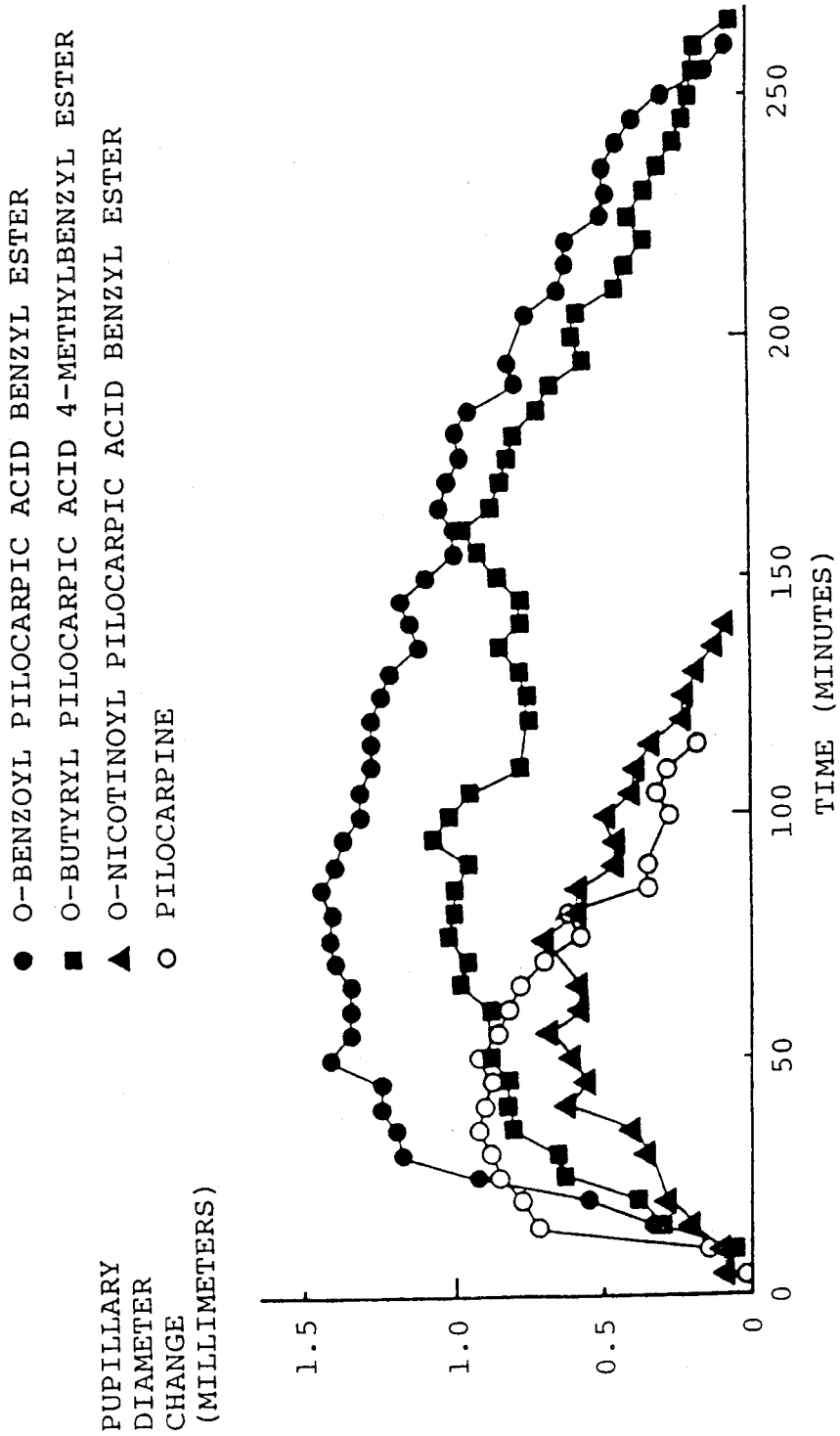

PILOCARPINE PRODRUGS

BACKGROUND OF THE INVENTION

1. Field of the Invention

The present invention relates to novel transient prodrug forms of pilocarpine useful in the treatment of glaucoma, to methods for preparing the prodrug forms, to pharmaceutical compositions containing such prodrug forms, and to methods for using the prodrug forms.

For purposes of this specification, the term "prodrug" denotes a derivative of pilocarpic acid which derivative, when administered topically to the eye of warm-blooded animals, e.g. humans, is converted into the proven drug, i.e. pilocarpine, in the ocular tissue thereof.

The term "transient" indicates that the conversion of the prodrug forms proceeds in such a manner that the proven drug form (parent pilocarpine) is released, and the moieties split off remain nontoxic or are metabolized so that nontoxic metabolic products are produced.

These novel prodrug forms of pilocarpine are certain pilocarpic acid derivatives which possess a disirable high lipophilicity in comparison to the parent compound, pilocarpine.

2. Description of the Prior Art

A pharmaceutical and medical need exists for new and useful compounds indicated for the management of glaucoma in warm-blooded animals. This need exists because the compound of choice, pilocarpine, exhibits an extremely low ocular bioavailability per se and from pharmaceutical dosage forms; only 1-3% or less of an instilled pilocarpine dose gain access to the internal eye structure (cf., e.g. Lee & Robinson (1979) and references cited therein). This poor ability of pilocarpine to penetrate across the cornea is generally attributed to the low lipophilicity of the drug pilocarpine. Because of the low bioavailability, massive ophthalmic dosing is required in order to enable an antiglaucoma effective amount of pilocarpine to reach the interior of the eye, (cf. Lerman & Reininger (1971). This massive dosing and low ocular bioavailability give rise to concern about systemic toxicity since most of the applied pilocarpine is then available for systemic absorption from the nasolacrimal duct (cf. Patton & Francoeur (1978)). The systemic absorption of pilocarpine may lead to undesired side-effects, e.g. in those patients who display sensitivity to cholinergic agents.

Another serious problem associated with pilocarpine is its short duration of action. Upon instillation into the eye, the duration of lowering of the intraocular pressure caused by pilocarpine lasts only for about 3 h. As a consequence thereof, the frequency of administration is at an inconvenient 3 to 8 times per day. Patient compliance with such treatment regimens is poor, and failure to comply is likely to contribute to inadequate pressure control and deterioration of vision (cf. Norell (1980); Norell & Granström (1980)).

Furthermore, the frequent administration of massive amounts of pilocarpine is associated with transient peaks of high drug concentration in the eye which in turn result in undesirable side-effects such as induced myopia and miosis. Since these side-effects are dose-related, the development of means to achieve a low-level, prolonged-effect therapy would represent a major advantage (cf. Lerman & Reininger (1971); Shell & Baker (1974)).

In view of the foregoing, it is quite obvious that a serious need exists for improved forms of pilocarpine which will overcome the aforementioned disadvantages. From the foregoing, it also appears that successful pilocarpine forms should exhibit a high lipophilicity in order to enable an efficient penetration through the corneal membrane, should be converted to the active pilocarpine once the corneal barrier has been passed, and finally should lead to a controlled release and prolonged duration of action of pilocarpine.

SUMMARY OF THE INVENTION

The above-discussed desirable attributes are possessed by pilocarpine prodrug derivatives according to the present invention which may be administered topically like pilocarpine and which, upon administration, once they reach the desired site of therapeutic after passage of the corneal barrier will be converted into the active parent pilocarpine resulting in therapeutic concentrations of pilocarpine and eliciting, albeit more efficiently and prolongedly, the same pharmacodynamic effect as would be elicited upon administration of the known parent pilocarpine.

Although the need for pilocarpine prodrugs with these desirable attributes has been generally recognized (cf., e.g. Lee & Robinson (1979)), the only previously described prodrug types are some quaternary ammonium salts of pilocarpine (cf. Bodor, U.S. Pat. No. 4,061,722). These compounds differ considerably from the compounds of the present invention.

The pilocarpine prodrugs of the present invention are pilocarpic acid derivatives. While it is generally known that pilocarpic acid can undergo a partial ring-closure to pilocarpine in acidic solution (pH 1-3), but not at physiological pH values (pH 7-7.5) or at basic pH, no information has existed about the reactivity of the hitherto unknown pilocarpic acid esters and other derivatives of the present invention. The present inventors have discovered that such pilocarpic acid derivatives, especially various types of esters, although being stable in acidic solutions (pH 3-4), undergo ring-closure with formation of pilocarpine in neutral and basic solutions, in other words, under conditions which prevail in the eye tissues. It has further been discovered that certain pilocarpic acid derivatives (in the following referred to as double prodrug forms of pilocarpine), although readily undergoing conversion into pilocarpine in vivo, possess an in vitro stability in aqueous solutions of pH greater than 4-5 that is comparable to or higher than that of pilocarpine.

The invention relates to compounds of the formula I

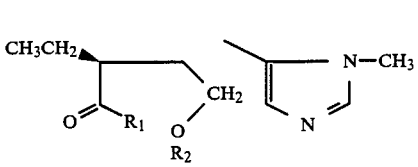

wherein $R_1$ is a group of the formula II $$R_3-X-$$  II wherein R₃ is alkyl; phenyl; phenyl substituted with halogen, lower alkyl, hydroxy, lower alkoxy, or phenoxy; phenyl-lower alkyl in which the phenyl group may be substituted with halogen, lower alkyl, hydroxy, lower alkoxy, or phenoxy; or phenyl-lower alkenyl in which the phenyl group may be substituted with halogen, lower alkyl, hydroxy, lower alkoxy or phenoxy; and X is oxygen or sulfur; or R₁ is a group of the formula III

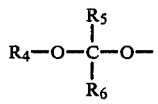

wherein R₄ has the same meaning as R₃ as defined above; or R₄ is a group of the formula IV

wherein R₇ has the same meaning as R₃ as defined above; or R₇ is an aromatic 5- or 6-membered heterocyclic ring containing one or two heteroatoms selected from the group consisting of nitrogen, oxygen, and sulfur; and wherein R₅ and R₆ are the same or different and each represent hydrogen or have the same meaning as R₃ as defined above;
or R₁ is a group of the formula V

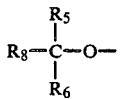

wherein R₅ and R₆ are as defined above and R₈ is polyhalogenated lower alkyl or a group of the formula VI

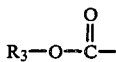

wherein R₃ is as defined above;
or R₁ is a group of the formula VII

wherein R₁₀ and R₁₁ together with the adjacent nitrogen atom form a 5- or 6-membered heterocyclic ring, which in addition to the nitrogen may contain one or two further heteroatoms selected from the group consisting of nitrogen, oxygen, and sulfur;
or R₁ is a group of the formula VIII

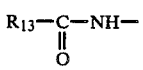

wherein R₁₃ is a group of the formula II, wherein R₃ and X are as defined above; or R₁₃ is a group of the formula VIIa

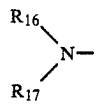

wherein R₁₆ and R₁₇ are the same or different and each represent hydrogen or have the same meaning as R₃ as defined above; or R₁₃ is a group of the formula VII, wherein R₁₀ and R₁₁ are as defined above;
or R₁ is a group of the formula IX

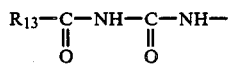

wherein R₁₃ is as defined above;
and R₂ is hydrogen or a group of the formula IV, wherein R₇ is as defined above;
or R₂ is a group of the formula VI, wherein R₃ is as defined above;
and salts thereof.

A most important characteristic of the prodrug derivatives of the formula I is that by appropriate selection of R₁ and optionally R₂ it is feasible to obtain prodrug forms of pilocarpine with varying physicochemical properties, such as lipophilicity, rate of pilocarpine formation, and in vitro stability (shelf life), and hence to control, modify, and optimize the ocular absorption and delivery of pilocarpine and its duration of action as well as its overall activity characteristics.

Accordingly, the present invention provides novel prodrug forms of pilocarpine which prodrugs, or transient derivatives, possess increased lipid solubility and enhanced ophthalmic absorption and prolonged action when administered to the ophthalmic membrane of a warm-blooded animal. Upon ophthalmic administration to a warm-blooded animal, pilocarpine prodrugs of the invention will be converted into the active parent pilocarpine (cf. Scheme 1 below) in therapeutic concentrations and will elicit the pharmacodynamic and therapeutically useful responses of their parent pilocarpine molecule more efficiently and prolongedly.

Scheme 1

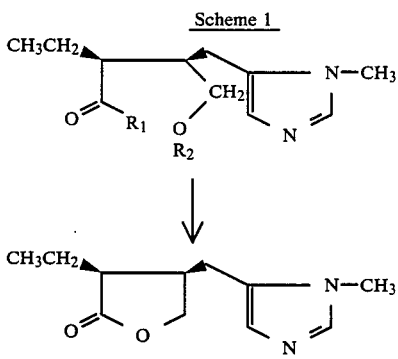

In the literature (Koda, et al. (1973)) is described the preparation of certain derivatives of pilocarpic acid, among these a few simple amides, viz. the amide, the N-methylamide and the N-isopropylamide. The reference in question, however, concerns a study of the cholinergic effect of pilocarpine and of the above-mentioned pilocarpine analogues after parenteral administration. The objective was to investigate the nature of the cholinergic receptor and the geometrical functional criteria for the cholinergic effect of a given compound. Thus, it is in no way implied that the compounds investigated have any prodrug activity whatsoever, and cyclization into pilocarpine is neither explicitly nor implicitly mentioned.

DETAILED DESCRIPTION OF THE INVENTION

The salts of the compounds of the formula I include any pharmaceutically acceptable acid addition salts. This term as used herein generally includes the non-toxic acid addition salts of compounds of the formula I, formed with non-toxic inorganic or organic acids. For example, the salts include salts with inorganic acids, such as hydrochloric, hydrobromic, sulfuric, sulfamic, nitric, phosphoric and the like; and the salts with organic acids such as acetic, propionic, succinic, fumaric, maleic, tartaric, citric, glycolic, stearic, lactic, malic, pamoic, ascorbic, phenylacetic, glutamic, benzoic, salicylic, sulfonic, sulfanilic, and the like.

In the present context, the term "alkyl" designates $C_{1-8}$ alkyl which may be straight or branched, such as methyl, ethyl, propyl, isopropyl, butyl, tert.butyl, pentyl, hexyl, heptyl, or octyl. Among the alkyl groups, lower alkyl groups are preferred. The term "lower alkyl" designates $C_{1-4}$ alkyl which may be straight or branched, such as methyl, ethyl, propyl, isopropyl, butyl, or tert.butyl. The term "phenyl-lower alkyl" designates a lower alkyl group (as herein defined) which, in turn, is substituted with a phenyl group. Preferred phenyl-lower alkyl are benzyl, 1- and 2-phenylethyl, 1-, 2-, and 3-phenylpropyl, and 1-methyl-1-phenylethyl. The term "phenyl-lower alkenyl" designates a $C_{2-5}$-monounsaturated aliphatic hydrocarbon group which may be straight or branched, such as propenyl, butenyl or pentenyl, and which in turn is substituted with a phenyl group. Preferred phenyl-lower alkenyl groups are phenyl-substituted propen(2)-yl optionally substituted with methyl or ethyl, such as 3-phenylpropen(2)-yl (both E and Z forms), 2-methyl-3-phenylpropen(2)-yl (both E and Z form), and 3-phenylbuten(2)-yl (both E and Z forms). The term "lower alkoxy" designates oxy to which is attached a lower alkyl group as defined above; preferred alkoxy groups are methoxy and ethoxy. The term "halogen" designates F, Cl, Br or I; Cl is preferred. Where phenyl groups are substituted with e.g. halogen, lower alkyl, hydroxy, lower alkoxy, or phenoxy, they may be mono-, di-, or trisubstituted, and when they are di- or trisubstituted, the substituents may be the same or different. The term "polyhalogenated lower alkyl" designates lower alkyl (as defined above) substituted with two or more halogen atoms, which may be the same or different. A preferred example of polyhalogenated lower alkyl is trichloromethyl. When, in the formula IV, $R_7$ is an aromatic 5- or 6-membered heterocyclic ring containing one or two hetero atoms selected from the group consisting of nitrogen, oxygen, and sulphur, this may, for instance, be 2-, 3-, or 4-pyridinyl, 2-, or 3-thienyl, 2-, 4-, or 5-thiazolyl, 2-, 4- or 5-oxazolyl, 2-imidazolyl, 5-isoxazolyl, 5-isothiazolyl, 2-furanyl, 2-, or 5-pyrimidinyl, 5-[1,3]oxazinyl, or 5-[1,3]thiazinyl. When, in the formula VII, $R_{10}$ and $R_{11}$ together with the adjacent nitrogen atom form a 5- or 6-membered heterocyclic ring which in addition to the nitrogen may contain one or two further hetero atoms selected from the group consisting of nitrogen, oxygen, and sulfur, it may, for instance, be 1-piperidinyl, 1-imidazolyl, 1-pyrazolyl, morpholinyl, 1-piperazinyl and thiomorpholinyl.

As examples of compounds of formula I may be mentioned compounds in which $R_2$ is as defined above, and $R_1$ is one of the following groups ("groups a"):

methoxy
butyloxy
octyloxy
phenoxy
4-chlorophenoxy
4-methylphenoxy
4-hydroxyphenoxy
4-methoxyphenoxy
benzyloxy
4-chlorobenzyloxy
4-methylbenzyloxy
4-bromobenzyloxy
4-tert.butylbenzyloxy
4-methoxybenzyloxy
4-hydroxybenzyloxy
4-phenoxybenzyloxy
4-fluorobenzyloxy
3-chlorobenzyloxy
2-chlorobenzyloxy
2,4-dichlorobenzyloxy
3,4-dimethylbenzyloxy
2,6-dimethylbenzyloxy
3,4-dihydroxybenzyloxy
3-methoxybenzyloxy
3-methylbenzyloxy
2-methoxybenzyloxy
2-methylbenzyloxy
3,4-dimethoxybenzyloxy
acetyloxymethyloxy
pivaloyloxymethyloxy
2-ethylbutyryloxymethyloxy
methoxymethyloxy
1-piperidinyl
1-imidazolyl
1-pyrazolyl
1-pyrrolyl
methyloxycarbonylamino
ethyloxycarbonylamino
benzyloxycarbonylamino
ureido
3,3-dimethylureido
3-ethoxycarbonylureido
1-(butyloxycarbonyl)ethyloxy
butyloxycarbonylmethyloxy
1-(octanyloxycarbonyl)ethyloxy
octanyloxycarbonylmethyloxy
1-methyl-1-trichloromethylethyloxy
1-(phenyl)ethyloxy
1-(4-methylphenyl)ethyloxy
1-(4-chlorophenyl)ethyloxy
1-(4-methoxyphenyl)ethyloxy
1-(4-hydroxyphenyl)ethyloxy
1-(4-tert.butylphenyl)ethyloxy
1-(2,4-dimethylphenyl)ethyloxy
1-(2,6-dimethylphenyl)ethyloxy
1-(2-methylphenyl)ethyloxy
2-(phenyl)ethyloxy
1-(phenyl)propyloxy
1-methyl-1-phenylethyloxy
1-methyl-1-(4-methylphenyl)ethyloxy
1-methyl-1-(4-chlorophenyl)ethyloxy
1-methyl-1-(4-methoxyphenyl)ethyloxy
2-(phenyl)propyloxy 3-(phenyl)propyloxy
4-(phenyl)butyloxy
2-(4-chlorphenyl)ethyloxy
2-(4-methylphenyl)ethyloxy
2-(4-methoxyphenyl)ethyloxy
3-(phenyl)propen(2)-yloxy (E and Z)
3-(4-chlorophenyl)propen(2)-yloxy (E and Z)
3-(4-methylphenyl)propen(2)-yloxy (E and Z)
3-(4-methoxyphenyl)propen(2)-yloxy (E and Z)
3-(phenyl)buten(2)-yloxy (E and Z)
3-(4-chlorophenyl)buten(2)-yloxy (E and Z)
3-(4-methylphenyl)buten(2)-yloxy (E and Z)
3-(4-methoxyphenyl)buten(2)-yloxy (E and Z)
benzylthio
and salts thereof.

It is preferred that X is oxygen because of the generally better stability in solution of esters as opposed to thioesters.

Because they generally more readily undergo ring-closure at physiological pH, preferred compounds of the invention are compounds in which $R_1$ is a group such that the compounds of the formula I are ester type compounds, in other words, $R_1$ is a group of the formulas II (where X is oxygen), III, or V as defined above, and $R_2$ is as defined above.

Examples of such compounds are compounds in which $R_2$ is as defined above, and $R_1$ is one of the following groups ("groups b"):
methoxy
phenoxy
4-chlorophenoxy
4-methylphenoxy
4-hydroxyphenoxy
4-methoxyphenoxy
benzyloxy
4-chlorobenzyloxy
4-methylbenzyloxy
4-bromobenzyloxy
4-tert.butylbenzyloxy
4-methoxybenzyloxy
4-hydroxybenzyloxy
4-phenoxybenzyloxy
4-fluorobenzyloxy
3-chlorobenzyloxy
2-chlorobenzyloxy
2,4-dichlorobenzyloxy
3,4-dimethylbenzyloxy
2,6-dimethylbenzyloxy
3-methoxybenzyloxy
3-methylbenzyloxy
2-methoxybenzyloxy
2-methylbenzyloxy
3,4-dimethoxybenzyloxy
acetyloxymethyloxy
pivaloyloxymethyloxy
2-ethylbutyryloxymethyloxy
methoxymethyloxy
1-(butyloxycarbonyl)ethyloxy
butyloxycarbonylmethyloxy
1-(octanyloxycarbonyl)ethyloxy
octanyloxycarbonylmethyloxy
1-methyl-1-trichloromethylethyloxy
1-(phenyl)ethyloxy
1-(4-methylphenyl)ethyloxy
1-(4-chlorophenyl)ethyloxy
1-(4-methoxyphenyl)ethyloxy
1-(4-hydroxyphenyl)ethyloxy
1-(4-tert.butylphenyl)ethyloxy
1-(2,4-dimethylphenyl)ethyloxy
1-(2,6-dimethylphenyl)ethyloxy
1-(2-methylphenyl)ethyloxy
2-(phenyl)ethyloxy
1-(phenyl)propyloxy
1-methyl-1-phenylethyloxy
1-methyl-1-(4-methylphenyl)ethyloxy
1-methyl-1-(4-chlorophenyl)ethyloxy
1-methyl-1-(4-methoxyphenyl)ethyloxy
2-(phenyl)propyloxy
3-(phenyl)propyloxy
4-(phenyl)butyloxy
2-(4-chlorphenyl)ethyloxy
2-(4-methylphenyl)ethyloxy
2-(4-methoxyphenyl)ethyloxy
3-(phenyl)propen(2)-yloxy (E and Z)
3-(4-chlorophenyl)propen(2)-yloxy (E and Z)
3-(4-methylphenyl)propen(2)-yloxy (E and Z)
3-(4-methoxyphenyl)propen(2)-yloxy (E and Z)
3-(phenyl)buten(2)-yloxy (E and Z)
3-(4-chlorophenyl)buten(2)-yloxy (E and Z)
3-(4-methylphenyl)buten(2)-yloxy (E and Z)
3-(4-methoxyphenyl)buten(2)-yloxy (E and Z)
and salts thereof.

More preferred compounds of the invention are compounds in which $R_1$ is a group of the formula II'

$$R'_3-O- \qquad \text{II'}$$

wherein $R'_3$ is phenyl-lower alkyl in which the phenyl group may be substituted with halogen, lower alkyl, hydroxy, lower alkoxy, or phenoxy; and $R_2$ is as defined above; and salts thereof. Compounds of this class undergo ring-closure to pilocarpine in quantitative amounts at rates which are surprisingly high at physiological pH.

Examples of such compounds are compounds in which $R_1$ is one of the following groups ("groups c"):
benzyloxy
3-chlorobenzyloxy
4-chlorobenzyloxy
2-methylbenzyloxy
4-methylbenzyloxy
4-bromobenzyloxy
4-tert.butylbenzyloxy
4-methoxybenzyloxy
4-hydroxybenzyloxy
4-phenoxybenzyloxy
4-fluorobenzyloxy
2,6-dimethylbenzyloxy
1-(phenyl)ethyloxy
1-(4-chlorophenyl)ethyloxy
1-(4-methylphenyl)ethyloxy
2-(phenyl)ethyloxy
1-(phenyl)propyloxy 1-methyl-1-(4-methylphenyl)ethyloxy
1-methyl-1-(4-chlorophenyl)ethyloxy
2-(4-chlorphenyl)ethyloxy
2-(4-methylphenyl)ethyloxy
and salts thereof.

Compounds of the invention in which $R_2$ in the general formula I is different from hydrogen may be considered double prodrugs of pilocarpine. It is believed that after ophthalmic administration of these double prodrug compounds, enzymes within the eye (e.g. corneal enzymes) will cleave the compounds into pilocarpic acid derivatives (formula I, $R_2$=hydrogen) which then undergo a non-enzymatic cyclization to yield pilocarpine. Compounds of this type have the major advantages that they possess a very high in vitro stability and produce a very prolonged miotic activity. The latter property is believed to be due to the special two-step mechanism of their conversion into pilocarpine.

In accordance with this, preferred compounds of the formula I are compounds ("compounds A") in which $R_2$ is different from hydrogen, that is, $R_2$ is a group of the formula IV, wherein $R_7$ is as defined above; or $R_2$ is a group of the formula VI, wherein $R_3$ is as defined above.

As examples of such compounds (A) may be mentioned compounds in which $R_1$ is a group selected from the groups a specified above and $R_2$ is one of the following groups ("groups a"):

picolyl
2-thienoyl
nicotinoyl
5-pyrimidinoyl
isonicotinoyl
acetyl
propionyl
butyryl
hexanoyl
octanoyl
benzoyl
4-chlorobenzoyl
4-methylbenzoyl
4-methoxybenzoyl
2-methylbenzoyl
2-chlorobenzoyl
3-methylbenzoyl
2,6-dimethylbenzoyl
2,6-dimethoxybenzoyl
2,4-dichlorobenzoyl
4-ethoxybenzoyl
4-hydroxybenzoyl
4-fluorobenzoyl
4-phenoxybenzoyl
phenylacetyl
3-phenylpropionyl
2-phenylpropionyl
2-phenylbutyryl
4-phenylbutyryl
4-chlorophenylacetyl
4-methylphenylacetyl
4-methoxyphenylacetyl
4-hydroxyphenylacetyl
2,4-dichlorophenylacetyl
cinnamoyl
4-methylcinnamoyl
4-chlorocinnamoyl
methoxycarbonyl
ethoxycarbonyl
butoxycarbonyl
hexyloxycarbonyl
octyloxycarbonyl
phenoxycarbonyl
4-chlorophenoxycarbonyl
4-methylphenoxycarbonyl
4-methoxyphenoxycarbonyl
benzyloxycarbonyl
4-chlorobenzyloxycarbonyl
4-methylbenzyloxycarbonyl
4-methoxybenzyloxycarbonyl
1-phenylethyloxycarbonyl
2-phenylethyloxycarbonyl
and salts thereof.

Among the compounds A (in which $R_2$ is different from hydrogen), preferred compounds are such ("compounds B") in which $R_1$ is a group of the formulas II (where X is oxygen), III, or V as defined above, and $R_2$ is a group of the formula IV, wherein $R_7$ is as defined above; or $R_2$ is a group of the formula VI, wherein $R_3$ is as defined above, and salts thereof.

Examples of such compounds (B) are compounds in which $R_1$ is a group selected from the groups b specified above, and $R_2$ is a group selected from groups α above, and salts thereof.

Among the compounds B, preferred compounds are such ("compounds C") in which $R_2$ is a group of the formula IV wherein $R_7$ is as defined above, and salts thereof.

Examples of such compounds (C) are compounds in which $R_1$ is a group selected from the groups b specified above, and $R_2$ is a group selected from the following groups ("groups β"):

picolyl
2-thienoyl
nicotinoyl
5-pyrimidinoyl
isonicotinoyl
acetyl
propionyl
butyryl
hexanoyl
octanoyl
benzoyl
4-chlorobenzoyl
4-methylbenzoyl
4-methoxybenzoyl
2-methylbenzoyl
2-chlorobenzoyl
3-methylbenzoyl
2,6-dimethylbenzoyl
2,6-dimethoxybenzoyl
2,4-dichlorobenzoyl
4-ethoxybenzoyl
4-hydroxybenzoyl
4-fluorobenzoyl
4-phenoxybenzoyl
phenylacetyl
3-phenylpropionyl
2-phenylpropionyl
2-phenylbutyryl
4-phenylbutyryl
4-chlorophenylacetyl
4-methylphenylacetyl
4-methoxyphenylacetyl
4-hydroxyphenylacetyl
2,4-dichlorophenylacetyl
cinnamoyl
4-methylcinnamoyl
4-chlorocinnamoyl
and salts thereof.

Among the compounds C, preferred compounds are such ("compounds D") in which $R_1$ is a group of the formula II' wherein $R'_3$ is as defined above, and $R_2$ is a group of the formula IV, wherein $R_7$ is as defined above, or $R_2$ is a group of the formula VI, wherein $R_3$ is as defined above, and salts thereof.

Examples of such compounds (D) are compounds in which $R_1$ is a group selected from the groups c specified above, and $R_2$ is a group selected from groups α specified above.

Among the compounds D, preferred compounds are such ("compounds E") in which $R_1$ is a group of the formula II' wherein $R'_3$ is as defined above and $R_2$ is a group of the formula IV wherein $R_7$ is as defined above, and salts thereof.

Examples of such compounds (E) are compounds in which $R_1$ is a group selected from the groups c specified above, and $R_2$ is a group selected from the groups $\beta$ specified above.

Among the compounds E, preferred compounds are such ("compounds F") in which $R_1$ is a group of the formula II' wherein $R'_3$ is as defined above, and $R_2$ is a group of the formula IV wherein $R_7$ is alkyl; phenyl; phenyl substituted with halogen, lower alkyl, hydroxy, lower alkoxy, or phenoxy; nicotinoyl or isonicotinoyl; and salts thereof.

Examples of such compounds (F) are compounds in which $R_1$ is a group selected from the groups c specified above, and $R_2$ is one of the following groups:
nicotinoyl
isonicotinoyl
acetyl
propionyl
butyryl
hexanoyl
octanoyl
benzoyl
4-chlorobenzoyl
4-methylbenzoyl
4-methoxybenzoyl
2-methylbenzoyl
2-chlorobenzoyl
3-methylbenzoyl
2,6-dimethylbenzoyl
2,6-dimethoxybenzoyl
2,4-dichlorobenzoyl
4-ethoxybenzoyl
4-hydroxybenzoyl
4-fluorobenzoyl
4-phenoxybenzoyl
and salts thereof.

Among the compounds F, preferred compounds are such in which $R_1$ is a group of the formula II' wherein $R'_3$ is as defined above, and $R_2$ is acetyl, propionyl, butyryl, or benzoyl.

Examples of such compounds are compounds in which $R_1$ is selected from the groups c specified above, and $R_2$ is acetyl, propionyl, butyryl, or benzoyl.

Very preferred compounds of the invention are compounds in which $R_1$ is benzyloxy, 2-phenylethyloxy, 4-chlorobenzyloxy, 4-methylbenzyloxy, or 4-tert.butylbenzyloxy, and $R_2$ is hydrogen or, in particular, acetyl, propionyl, butyryl, or benzoyl.

Specific examples of preferred compounds of the formula I are:
Pilocarpic acid benzyl ester
Pilocarpic acid 4-chlorobenzyl ester
Pilocarpic acid 3-chlorobenzyl ester
Pilocarpic acid 4-methylbenzyl ester
Pilocarpic acid 4-methoxybenzyl ester
Pilocarpic acid 4-tert.butylbenzyl ester
Pilocarpic acid 4-phenoxybenzyl ester
Pilocarpic acid 2-methylbenzyl ester
Pilocarpic acid 1-phenylethyl ester
O-Benzoyl pilocarpic acid benzyl ester
O-Benzoyl pilocarpic acid 4-chlorobenzyl ester
O-Benzoyl pilocarpic acid 3-chlorobenzyl ester
O-Benzoyl pilocarpic acid 4-methylbenzyl ester
O-Benzoyl pilocarpic acid 4-methoxybenzyl ester
O-Benzoyl pilocarpic acid 4-tert.butylbenzyl ester
O-Benzoyl pilocarpic acid 4-phenoxybenzyl ester
O-Benzoyl pilocarpic acid 2-methylbenzyl ester
O-Benzoyl pilocarpic acid 1-phenylethyl ester
O-2-Methylbenzoyl pilocarpic acid benzyl ester
O-2-Methylbenzoyl pilocarpic acid 4-chlorobenzyl ester
O-2-Methylbenzoyl pilocarpic acid 3-chlorobenzyl ester
O-2-Methylbenzoyl pilocarpic acid 4-methylbenzyl ester
O-2-Methylbenzoyl pilocarpic acid 4-methoxybenzyl ester
O-2-Methylbenzoyl pilocarpic acid 4-tert.butylbenzyl ester
O-2-Methylbenzoyl pilocarpic acid 4-phenoxybenzyl ester
O-2-Methylbenzoyl pilocarpic acid 2-methylbenzyl ester
O-2-Methylbenzoyl pilocarpic acid 1-phenylethyl ester
O-2,6-Dimethylbenzoyl pilocarpic acid benzyl ester
O-2,6-Dimethylbenzoyl pilocarpic acid 4-chlorobenzyl ester
O-2,6-Dimethylbenzoyl pilocarpic acid 3-chlorobenzyl ester
O-2,6-Dimethylbenzoyl pilocarpic acid 4-methylbenzyl ester
O-2,6-Dimethylbenzoyl pilocarpic acid 4-methoxybenzyl ester
O-2,6-Dimethylbenzoyl pilocarpic acid 4-tert.butylbenzyl ester
O-2,6-Dimethylbenzoyl pilocarpic acid 4-phenoxybenzyl ester
O-2,6-Dimethylbenzoyl pilocarpic acid 2-methylbenzyl ester
O-2,6-Dimethylbenzoyl pilocarpic acid 1-phenylethyl ester
O-Phenylacetyl pilocarpic acid benzyl ester
O-Phenylacetyl pilocarpic acid 4-chlorobenzyl ester
O-Phenylacetyl pilocarpic acid 3-chlorobenzyl ester
O-Phenylacetyl pilocarpic acid 4-methylbenzyl ester
O-Phenylacetyl pilocarpic acid 4-methoxybenzyl ester
O-Phenylacetyl pilocarpic acid 4-tert.butylbenzyl ester
O-Phenylacetyl pilocarpic acid 4-phenoxybenzyl ester
O-Phenylacetyl pilocarpic acid 2-methylbenzyl ester
O-Phenylacetyl pilocarpic acid 1-phenylethyl ester
O-Acetyl pilocarpic acid benzyl ester
O-Acetyl pilocarpic acid 4-chlorobenzyl ester
O-Acetyl pilocarpic acid 3-chlorobenzyl ester
O-Acetyl pilocarpic acid 4-methylbenzyl ester
O-Acetyl pilocarpic acid 4-methoxybenzyl ester
O-Acetyl pilocarpic acid 4-tert.butylbenzyl ester
O-Acetyl pilocarpic acid 4-phenoxybenzyl ester
O-Acetyl pilocarpic acid 2-methylbenzyl ester
O-Acetyl pilocarpic acid 1-phenylethyl ester
O-Propionyl pilocarpic acid benzyl ester
O-Propionyl pilocarpic acid 4-chlorobenzyl ester
O-Propionyl pilocarpic acid 3-chlorobenzyl ester
O-Propionyl pilocarpic acid 4-methylbenzyl ester
O-Propionyl pilocarpic acid 4-methoxybenzyl ester
O-Propionyl pilocarpic acid 4-tert.butylbenzyl ester
O-Propionyl pilocarpic acid 4-phenoxybenzyl ester
O-Propionyl pilocarpic acid 2-methylbenzyl ester
O-Propionyl pilocarpic acid 1-phenylethyl ester
O-Butyryl pilocarpic acid benzyl ester
O-Butyryl pilocarpic acid 4-chlorobenzyl ester
O-Butyryl pilocarpic acid 3-chlorobenzyl ester O-Butyryl pilocarpic acid 4-methylbenzyl ester
O-Butyryl pilocarpic acid 4-methoxybenzyl ester
O-Butyryl pilocarpic acid 4-tert.butylbenzyl ester
O-Butyryl pilocarpic acid 4-phenoxybenzyl ester
O-Butyryl pilocarpic acid 2-methylbenzyl ester
O-Butyryl pilocarpic acid 1-phenylethyl ester
and salts thereof.

Specific examples of especially preferred compounds are O-benzoyl pilocarpic acid 4-methylbenzyl ester, O-benzoyl pilocarpic acid benzyl ester, O-benzoyl pilocarpic acid 4-chlorobenzyl ester, O-butyryl pilocarpic acid 4-methylbenzyl ester, O-phenylacetyl pilocarpic acid benzyl ester, O-acetyl pilocarpic acid 4-methylbenzyl ester, O-butyryl pilocarpic acid benzyl ester and O-propionyl pilocarpic acid benzyl ester, and salts thereof.

A particularly preferred compound is O-benzoyl pilocarpic acid benzyl ester.

Compounds of the formula I may be administered per se, or in combination with any pharmaceutically appropriate inert ophthalmic vehicle or carrier system. The administered dose (either as a single dose, a daily dose, or other time-presented dose) depends on the requirements of the individual under treatment. The dosage administered is, therefore, not subject to specific limits. The dose of any compound of the formula I will typically be an anti-glaucoma effective amount, or, expressed in another way, an amount of the compound of the formula I which, inside the eye, produces an amount of pilocarpine that achieves the desired pharmacological response. Generally, the single medical dose for warm-blooded animals, which include humans and primates, will be in the range of approximately 0.005 mg to 4 mg, with 0.1 mg to 2 mg being preferred. The number of doses per day will be in the range of 1–5, preferably 2–4. The compounds of the formula I may be administered in the form of a pharmaceutical composition, which may be a liquid application form, such as a solution, a suspension, or an emulsion; an ointment; a cream; an aerosol; a polymeric or solid controlled-release or monitoring drug delivery device (such as a membrane or capsule-type delivery system); or a polymeric solution that gels upon ophthalmic instillation resulting in a controlled-release or monitoring drug delivery device or system.

In contrast to pilocarpine, the prodrug derivatives of the formula I are only slightly soluble in water in their free base forms. This property may be of great value and broaden the range of useful pharmaceutical dosage forms. Thus, as indicated above, aqueous suspensions prepared from the prodrug derivatives of the formula I, as well as capsule-type delivery systems based on lipophilic membranes surrounding the drug reservoir can be applied. Since pilocarpine is extremely water-soluble both in its free base form and in the form of various salts such means of dispensing pilocarpine itself are limited or impossible (vide e.g. Justin et al. (1981)).

The pharmaceutically appropriate inert vehicle or carrier systems for the ophthalmic administration of the compounds of the present invention are well-known to those skilled in the art of ophthalmic pharmaceutical formulations. Thus, pharmaceutically acceptable carriers for the preparation of eyedrops include conventional or common vehicle buffer systems, isotonic boric acid or borate solutions, isotonic saline vehicles, and the like, with or without polymers and/or viscosity altering additives such as hydroxypropyl cellulose, methylcellulose, polyvinylpyrrolidone, polyvinyl alcohol or polyacrylamide. Suitable carriers for the preparation of ophthalmic oil solutions of the compounds of this invention include arachis oil and other oils like castor and mineral oils. Further information concerning formulation of ophthalmic pharmaceutical preparations is found in the texts entitled "Remington's Pharmaceutical Sciences", Sixteenth Edition, 1980, and "Ophthalmic Drug Delivery Systems" (J. R. Robinson, Ed. (1980)) as well as to the paper by M. Justin et al. (1981).

The presently preferred administration form is an eyedrop solution.

An example of a typical method for preparing aqueous eyedrops containing a compound of the present invention is to dissolve the compound (e.g. as a water-soluble salt) in sterile water in a given concentration (e.g. 2–4%), optionally adjust the pH to e.g. 4–6 with a suitable buffer or with hydrochloric acid or sodium hydroxide, optionally add a preservative like phenethanol or chlorobutanol, optionally add a viscosity altering additive like methylcellulose, and sterilize the final solution by e.g. membrane filtration or autoclaving.

Due to the high in vitro stability of compounds of the formula I in which $R_2$ is different from hydrogen (cf. Table 2), aqueous solutions of such compounds, with shelf lives greater than 5 years may be prepared, even at pH values of 5–6.

An eyedrop preparation may also consist of the compound formulated as a sterile, solid preparation in an eyedrop container. Before dispensing, isotonic saline is added to dissolve the compound.

The compounds of the invention may be prepared by various methods. One method (a) comprises
reacting a salt of pilocarpic acid such as a metal salt, or a compound of the formula X, or a salt thereof

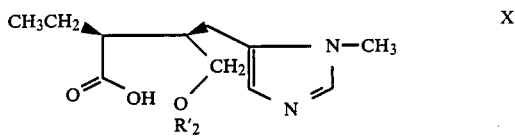

in which $R'_2$ is a group of the formula IV, wherein $R_7$ is as defined above; or $R'_2$ is a group of the formula VI, wherein $R_3$ is as defined above; or $R'_2$ is alkyl, especially tert.butyl; phenyl; or substituted phenyl, especially 2,4-dinitrophenyl; benzyl; benzyl substituted in the phenyl group with halogen, lower alkyl, hydroxy, lower alkoxy or nitro, especially 2-bromobenzyl or 2-nitrobenzyl; 4-toluenesulphonyl; picolyl; tetrahydropyranyl; or 1-benzyloxy-carbonylamino-2,2,2-trifluoroethyl;

with a compound of the formula XI

wherein $R_{14}$ has the same meaning as $R_3$ as defined above; or $R_{14}$ is a group of the formula XII

wherein $R_4$, $R_5$, and $R_6$ are as defined above; or $R_{14}$ is a group of the formula XIII

wherein $R_5$, $R_6$, and $R_8$ are as defined above; and Z is hydroxy or a leaving group; and then, when $R'_2$ is different from $R_2$, removing $R'_2$, and then, if desired, introducing a new group $R_2$.

As examples of leaving groups Z may be mentioned chlorine, bromine, iodine, and 4-toluenesulfonyl. The reaction is preferably performed in a solvent (e.g. a lower alcohol, toluene, N,N-dimethylformamide, or the like). In the reaction of a compound of the general formula X with a compound of the general formula XI, Z can also be hydroxy. When Z is hydroxy a dehydrating agent (e.g. N,N-dicyclohexylcarbodiimide) has to be present. The reaction is carried out at a temperature from 0° C. to the boiling point of the solvent, and for a period of time from 1 to 96 hours.

Another method (b) for preparing compounds of the invention comprises reacting a salt such as a metal salt of pilocarpic acid or a compound of the formula XIV or an acid addition salt thereof

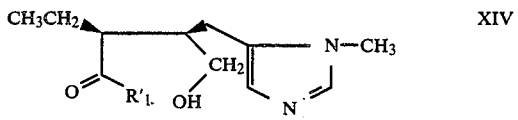

wherein $R'_1$ has the same meaning as $R_1$ as defined above in connection with formula I; or $R'_1$ is a group removable by hydrolysis or hydrogenation, of the formula XV

 XV wherein $R_{15}$ is benzyl substituted in the phenyl group with nitro; diphenylmethyl; phenacyl; trimethylsilyl; pentamethylbenzyl; phthalimidomethyl; 9-anthrylmethyl; picolyl; or phthaloyl; and X is oxygen or sulfur; with a compound of the formula XVI

 XVI wherein $R'_2$ is as defined above; and Y is hydroxy or a leaving group; and then, if $R'_1$ is different from $R_1$, removing the group $R'_1$ and introducing a group $R_1$; and then, when $R'_2$ is different from $R_2$, removing $R'_2$, and then, if desired, introducing a new group $R_2$.

The reaction is normally performed in a solvent such as chloroform, benzene, toluene or the like at a temperature in the range of $-15°$ C. to $100°$ C., preferably from $0°$ C. to $50°$ C., in the presence of a base (e.g. potassium carbonate, a sodium alcoholate or the like). In the reaction of a compound of the formula XIV with a compound of the formula XVI, Y can also be hydroxy. When Y is hydroxy, a dehydrating agent (e.g. N,N-dicyclohexylcarbodiimide) has to be present. The removal of the group $R'_1$ different from $R_1$ may be performed in a manner known per se, (e.g. by hydrolysis or hydrogenation), and a new group $R_1$ may be introduced in a manner described above under (a). Then, if $R'_2$ is different from $R_2$, $R'_2$ is removed in a manner known per se (e.g. by hydrolysis or hydrogenation), and, if desired, a new group $R_2$ may be introduced by a method as described above.

A third method (c) for preparing compounds of the invention comprises reacting pilocarpine or an acid addition salt thereof with a compound of the formula XVII $R_1H$  XVII wherein $R_1$ is as defined above in connection with formula I, and, if desired, introducing a new group $R_2$.

The reaction may be performed without or in a solvent such as chloroform, benzene, toluene, or the like, with or without an acid or base as catalyst, at a temperature from 20° C. to 150° C., preferably at a temperature in the range of 20° C. to 100° C. and for a period of time from a few hours to several days, normally from 2 to 20 hours. The introduction of a new group $R_2$ may be performed by the method (b) discussed above.

A further method (d) for preparing compounds of the invention comprises reacting a compound of the formula XVIII or a salt thereof

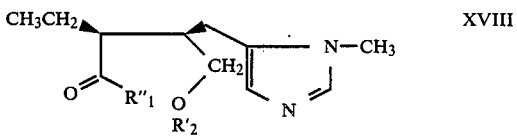 XVIII wherein $R''_1$ is hydroxy or a group $R_1$ as defined above in connection with formula I; or $R''_1$ is a leaving group; and $R'_2$ is as defined above; with a compound of the formula XVII wherein $R_1$ is as defined above in connection with formula I, with the proviso that $R_1$ in the formula XVII is different from $R''_1$ in the formula XVIII, and then, when $R'_2$ is different from $R_2$, removing $R'_2$ and, if desired, introducing a new group $R_2$.

The reaction is carried out without or in a solvent (e.g. chloroform benzene, toluene, acetone, or the like) and at a temperature from $-15°$ C. to the boiling point of the solvent or of the compound of the formula XVII, and for a period of time from 1 hour to 96 hours; when $R''_1$ is hydroxy a dehydrating agent (e.g. a carbodiimide) has to be present. The removal of $R'_2$ may be performed by, e.g., hydrolysis or hydrogenation. The introduction of a new group $R_2$ may be performed by the method (b) described above.

Salts of compounds of the formula I may be prepared by mixing an acid with a compound of the formula I in or without the presence of a solvent, preferably using a calculated amount of acid required to obtain a salt of the formula I.

The invention also relates to an advantageous method for preparing substantially pure salts of pilocarpic acid, which are useful intermediates in the preparation of the compounds of the formula I, and to the substantially pure salts per se. The salts are, in particular, alkali metal or alkaline earth metal salts of pilocarpic acid, preferably, the salt is the sodium salt.

The method comprises hydrolyzing pilocarpine in an aqueous medium with a strong base at a temperature of about 0° C.

The purity of these substantially pure salts of pilocarpic acid obtained in this manner is normally at least 85%, with less than 15% of the undesired salt of isopilocarpic acid. At such purity, the salt is directly useful as a starting material for the further synthesis which will result in a crude product from which the optically pure products of the general formula I may easily be separated, e.g. by recrystallization.

The temperature at which pilocarpine is hydrolyzed with a strong base in accordance with this aspect of the invention may, e.g., be 0°–5° C. The strong base may be an alkali metal or alkaline earth metal hydroxide such as sodium hydroxide and is, preferably, used in an excess, such as an excess of 3–20%, preferably 5–10%. The crude product with a purity of 85% to 90% may be further purified by recrystallization, resulting in a product containing less than 5% of isopilocarpic acid salt, preferably less than 2.5% of isopilocarpic acid salt.

According to the invention, it has been found that when working under the above-identified conditions, the two competing reactions, that is, hydrolysis to pilocarpic acid and epimerization to isopilocarpine, are balanced in a very favourable manner so that the epimerization is strongly depressed. If the ring-opening of pilocarpine is performed at higher temperatures, e.g. 25° C. to 50° C., the epimerization makes a greater contribution to the total degradation, thus resulting in the formation of a product with a considerably higher content of the corresponding isopilocarpic acid salt.

The invention also relates to further novel intermediates for preparing the compounds of the formula I. These novel intermediates are of the formula X

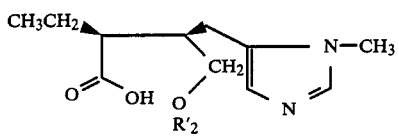

X in which R'₂ is as defined above, and salts thereof.

The compounds of the formula X or salts thereof may be prepared by reacting a salt such as a metal salt of pilocarpic acid or a compound of the formula XIV or an acid addition salt thereof

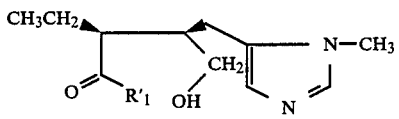

XIV wherein R'₁ is as defined above with a compound of the formula XVI

XVI wherein R'₂ and Y are defined as above; and then, if necessary, removing the group R'₁.

The reaction is normally performed in a solvent such as chloroform, benzene, toluene or the like at a temperature in the range of −15° C. to 100° C., preferably from 0° C. to 50° C., in the presence of a base (e.g. potassium carbonate, a sodium alcoholate or the like). In the reaction of a compound of the formula XIV with a compound of the formula XVI, Y can also be hydroxy. When Y is hydroxy, a dehydrating agent (e.g. N,N-dicyclohexylcarbodiimide) has to be present. The removal of the group R'₁ may be performed in a manner known per se, (e.g. by hydrolysis or hydrogenation).

The compounds of the formula X and salts thereof may also be prepared by hydrolyzing pilocarpine or a salt thereof with a base in the presence of a compound of the formula XVI, thus avoiding the need for isolating the pilocarpic acid salt. Expressed in another way, the pilocarpic acid salt is generated in situ and is further reacted without isolation.

DESCRIPTION OF THE DRAWINGS

FIG. 7 shows miosis-time profiles following the instillation of 25.0 μl of the pH-adjusted, isotonic solutions in equimolar concentrations (0.25% pilocarpine nitrate equivalent) of the compounds indicated.

Figure 1:
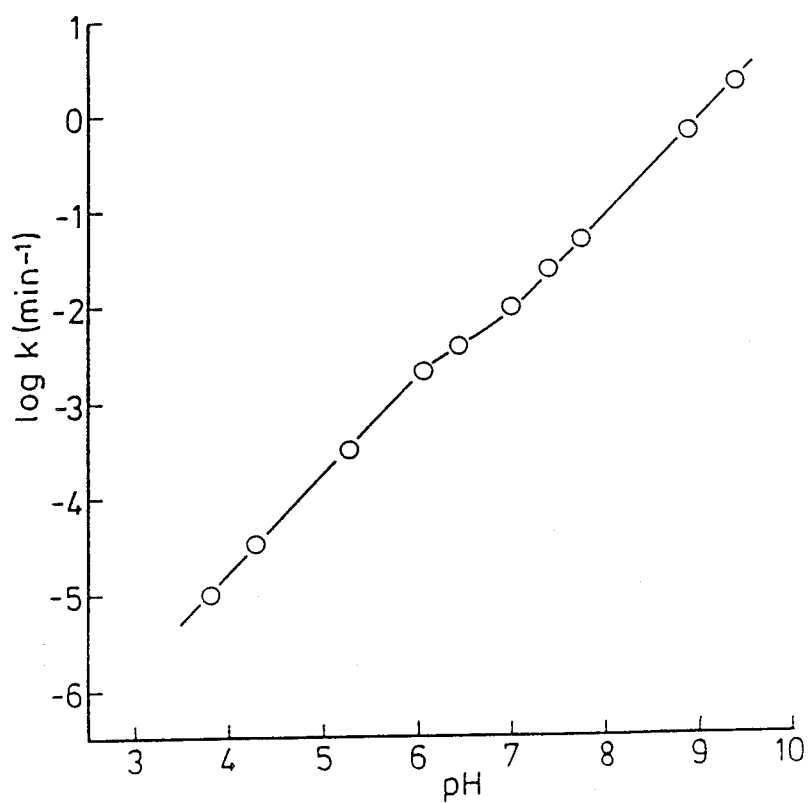
FIG. 1 shows a plot of the logarithm of the observed pseudo-first order rate constants against pH for the cyclization of 4-chlorobenzyl pilocarpic acid ester to pilocarpine in aqueous solution at 37° C.

The present invention is further illustrated by the following examples which, however, are not construed to be limiting. The examples especially illustrate the preferred embodiments of the invention.

EXAMPLE 1

Sodium Salt of Pilocarpic Acid

To a solution of pilocarpine hydrochloride (9.80 g, 40 mmol) in 20 ml of water, kept in an ice-water bath, was added 90 ml of 1M sodium hydroxide, cooled to about 0°–4° C., in three portions. The solution was allowed to stand at this temperature for about 1 hour. After neutralizing the excess of sodium hydroxide by adding 10 ml of 1M hydrochloric acid, the solution was evaporated under reduced pressure at 40° C. After drying in vacuo over phosphorous pentoxide, the resulting solid residue was slurried in 150 ml of ethanol and stirred for 15 minutes at 60° C. After cooling to 4° C., the insoluble sodium chloride was filtered off. The filtrate was evaporated in vacuo and the residue dried in vacuo over phosphorous pentoxide at ambient temperature, giving 9.3 g (88% yield) of pilocarpic acid sodium salt monohydrate. HPLC analysis of the compound performed as described in Bundgaard & Honoré Hansen (1982) revealed the presence of 10% of the sodium salt of isopilocarpic acid. (This material proved highly satisfactory as a starting material for the synthesis of pure pilocarpic acid esters).

A sample of the crude product prepared as above was purified by fractional crystallization from 2-propanol/acetonitrile/ether giving a product with a purity of 97.8% (i.e. containing 2.2% of the sodium salt of isopilocarpic acid as determined by HPLC as above). The purified product had a specific optical rotation $[\alpha]_D$ of +22.4 (water).

The capacity factors (k') stated in the following examples were determined by HPLC under the following conditions:

Column: 250 mm×4 mm LiChrosorb RP8 (Merck).
Solvent: Methanol/0.02M $KH_2PO_4$ (3:1 vol:vol).
Flow: 1.2 ml/min.
Detection: UV 215 nm.

EXAMPLE 2

Pilocarpic Acid Butyl Ester (formula I; $R_1$=butyloxy; $R_2$=hydrogen)

To a solution of 4 mmol of the sodium salt of pilocarpic acid, prepared as described in Example 1, in 60 ml of N,N-dimethylformamide was added 4 mmol of butyl bromide. The solution was stirred at room temperature overnight, poured into 75 ml of water and then extracted with two 75 ml portions of ethyl acetate. The combined ethyl acetate extracts were washed with 50 ml of water, 50 ml of 2% sodim bicarbonate solution and 50 ml of water. After drying with magnesium-sulfate, the ethyl acetate was evaporated under reduced pressure. The residue was crystallized from chloroform/petroleum ether to give 337 mg (30%) of ester. Mp 89°–90° C. The NMR-spectrum (in $CDCl_3$) was in agreement with the structure of the ester.

k': 0.63.

Analysis: Calculated for $C_{15}H_{26}N_2O_3$: C 63.80; H 9.28; N 9.92. Found: C 63.65; H 9.42; N 9.92.

EXAMPLE 3

Pilocarpic Acid Benzyl Ester (formula I; $R_1$=benzyloxy; $R_2$=hydrogen)

The ester was prepared from the sodium salt of pilocarpic acid and benzyl bromide by the procedure described in Example 2 and isolated in 31% yield. Mp 84°–85° C. The ester was hygroscopic.

k': 0.65.

Analysis: Calculated for $C_{18}H_{24}N_2O_3$, $0.2H_2O$: C 67.56; H 7.69; N 8.75. Found: C 67.51; H 7.46; N 8.78.

EXAMPLE 4

Pilocarpic Acid 4-Chlorobenzyl Ester (formula I; $R_1$=4-chlorobenzyloxy; $R_2$=hydrogen)

The ester was prepared from the sodium salt of pilocarpic acid and 4-chlorobenzyl chloride by the procedure described in Example 2. The crude product was recrystallized from ethyl acetate. Yield: 31%. Mp 106°–107° C.

k': 0.96.

Analysis: Calculated for $C_{18}H_{23}ClN_2O_3$: C 61.62; H 6.61; Cl 10.11; N 7.89. Found: C 61.71; H 6.64; Cl 10.05; N 7.91.

EXAMPLE 5

Pilocarpic Acid 4-Methylbenzyl Ester (formula I; $R_1$=4-methylbenzyloxy; $R_2$=hydrogen)

The ester was prepared from the sodium salt of pilocarpic acid and 4-methylbenzyl bromide by the procedure described in Example 2. The crude product was recrystallized from chloroform/petroleum ether and from ethyl acetate. Yield: 30%. Mp 107°–109° C.

k': 0.91.

Analysis: Calculated for $C_{19}H_{26}N_2O_3$: C 69.06; H 7.93; N 8.48. Found: C 68.77; H 7.88; N 8.53.

EXAMPLE 6

Pilocarpic Acid 2-Methylbenzyl Ester (formula I; $R_1$=2-methylbenzyloxy; $R_2$=hydrogen)

The ester was prepared from the sodium salt of pilocarpic acid and 2-methylbenzyl bromide by the procedure described in Example 2. The crude product was recrystallized from ether. Yield: 35%. Mp 57°–60° C.

k': 0.87.

Analysis: Calculated for $C_{19}H_{26}N_2O_3$: C 69.06; H 7.93; N 8.48. Found: C 68.77; H 7.84; N 8.39.

EXAMPLE 7

Pilocarpic Acid Benzyl Ester Fumarate Monohydrate

To a solution of pilocarpic acid benzyl ester (see Example 3) (158 mg, 0.5 mmol) in 3 ml of ethyl acetate was added a solution of fumaric acid (60 mg, 0.5 mmol) in a mixture of ethanol and ether. The solution was evaporated in vacuo and the residue was recrystallized twice from 2-propanol/petroleum ether yielding the title compound, mp. 77°–78° C.

k': 0.65.

Analysis: Calculated for $C_{22}H_{28}N_2O_7 \cdot H_2O$: C 58.66; H 6.71; N 6.23. Found: C 59.07; H 6.73; N 6.23.

EXAMPLE 8

Pilocarpic Acid Butyl Ester (formula I; $R_1$=butyloxy; $R_2$=hydrogen)

A mixture of pilocarpine hydrochloride (2.0 g) and conc. sulfuric acid (0.2 ml) in butanol (10 ml) was stirred at room temperature for 24 h and then kept at 60° C. for 2 h. After cooling, unreacted starting material was removed by filtration and calcium carbonate (1.5 g) was added to the filtrate. The mixture was filtered and the filtrate evaporated. Ether (20 ml) was added to the residue and the ethereal solution was washed with 10 ml of a 2% aqueous sodium bicarbonate solution and with 10 ml of water. After drying, the ether was removed in vacuo leaving the title compound (188 mg), shown by TLC, HPLC, and IR-spectroscopy to be identical to the compound prepared in Example 2.

EXAMPLE 9

Pilocarpic Acid 2-Phenylethyl Ester (formula I; $R_1$=2-phenylethoxy; $R_2$=hydrogen)

The ester was prepared from he sodium salt of pilocarpic acid and 2-phenylethyl bromide by the procedure described in Example 2. After one recrystallization from ether the yield was 22% and the mp. 66°–70° C. One further recrystallization from ethyl acetate/ether/petroleum ether raised the mp. to 74°–77° C.

k': 0.76.

Analysis: Calculated for $C_{19}H_{26}N_2O_3$: C 69.06; H 7.93; N 8.48. Found: C 68.48; H 7.92; N 8.32.

EXAMPLE 10

Pilocarpic Acid 4-tert.Butylbenzyl Ester (formula I; $R_1$=4-tert.butylbenzyloxy; $R_2$=hydrogen)

The ester was prepared from the sodium salt of pilocarpic acid and 4-tert.butylbenzyl bromide by the procedure described in Example 2. After one recrystallization from ether the yield was 18% and the mp. 61°-65° C. Recrystallizations from ether and ether/petroleum ether raised the mp. to 68°-69° C.

$k'$: 1.96.

Analysis: Calculated for $C_{22}H_{32}N_2O_3$: C 70.94; H 8.66; N 7.52. Found: C 70.55; H 8.84; N 7.52.

EXAMPLE 11

O-Benzoyl Pilocarpic Acid 4-Methylbenzyl Ester. Salt with 1.5 equivalent fumaric acid (formula I; $R_1$=4-methylbenzyloxy; $R_2$=benzoyl)

To a mixture of 661 mg (2 mmole) of pilocarpic acid 4-methylbenzyl ester (see Example 5) and potassium carbonate (345 mg; 2.5 mmole) in toluene (20 ml) was added three portions of benzoyl chloride (0.28 g; 2 mmole) over a period of 24 h. To the reaction mixture was added a 2% aqueous solution of sodium bicarbonate (20 ml) and the mixture was stirred at room temperature for 3 h. The layers were separated and the organic phase was washed twice with water, dried, and evaporated in vacuo leaving the crude O-benzoyl pilocarpic acid ester as an oil. Part of the oil (450 mg, 1 mmole) was dissolved in ether (15 ml) and a solution of fumaric acid in 2-propanol was added followed by petroleum ether. After standing overnight at 5° C. the title compound was isolated by filtration leaving 249 mg (42%). After recrystallization from 2-propanol/petroleum ether the compound melted at 86°-87° C.

$k'$: 3.39.

Analysis: Calculated for $C_{26}H_{30}N_2O_4.1.5$ fumaric acid: C 63.15; H 5.96; N 4.60. Found: C 62.95; H 6.06; N 4.58.

EXAMPLE 12

O-Acetyl Pilocarpic Acid 4-Methylbenzyl Ester. Salt with 1.5 equivalent fumaric acid (formula I; $R_1$=4-methylbenzyloxy; $R_2$=acetyl)

The compound was prepared from pilocarpic acid 4-methylbenzyl ester (see example 5) and acetyl chloride by the procedure described in Example 11. The title compound was recrystallized from 2-propanol/ether/petroleum ether.

Yield: 85%. Mp. 80°-81° C.

$k'$: 1.45.

Analysis: Calculated for $C_{21}H_{28}N_2O_4$, 1.5 fumaric acid: C 59.33; H 6.27; N 5.12. Found: C 59.23; H 6.32; N 5.10.

EXAMPLE 13

Pilocarpic Acid 1-Phenylethyl Ester (formula I; $R_1$=1-phenylethoxy; $R_2$=hydrogen)

The ester was prepared from the sodium salt of pilocarpic acid and α-methylbenzyl bromide by the procedure described in Example 2. The crude product was recrystallized from ethyl acetate.

Mp. 109°-110° C.

$k'$: 0.78.

Analysis: Calculated for $C_{19}H_{26}N_2O_3$: C 69.06; H 7.93; N 8.48. Found: C 68.58; H 7.88; N 8.32.

EXAMPLE 14

O-Benzoyl Pilocarpic Acid Benzyl Ester. Salt with 1.5 equivalent fumaric acid (formula I; $R_1$=benzyloxy; $R_2$=benzoyl)

The compound was prepared from pilocarpic acid benzyl ester (see Example 3) and benzoyl chloride by the procedure described in Example 11. The title compound was recrystallized from 2-propanol/ether/petroleum ether. Mp 88°-90° C.

$k'$: 2.70.

Analysis: Calculated for $C_{25}H_{28}N_2O_4.1.5$ fumaric acid: C 62.62; H 5.76; N 4.71. Found: C 62.66; H 5.79; N 4.68.

EXAMPLE 15

O-Benzoyl Pilocarpic Acid 4-Chlorobenzyl Ester. Salt with 1.5 equivalent fumaric acid (formula I; $R_1$=4-chlorobenzyloxy; $R_2$=benzoyl)

The compound was prepared form pilocarpic acid 4-chlorobenzyl ester (see Example 4) and benzoyl chloride by the procedure described in Example 11. The title compound was recrystallized from 2-propanol/ether/petroleum ether. Mp. 109°-111° C.

$k'$: 3.69.

Analysis: Calculated for $C_{25}H_{27}ClN_2O_4.1.5$ fumaric acid: C 59.19; H 5.29; Cl 5.64; N 4.45. Found: C 59.10; H 5.46; Cl 5.56; N 4.41.

EXAMPLE 16

O-Benzoyl Pilocarpic Acid 2-Phenylethyl Ester. Salt with 1.5 equivalent fumaric acid.

(formula I; $R_1$=2-phenylethoxy; $R_2$=benzoyl)

The compound was prepared from pilocarpic acid 2-phenylethyl ester (see Example 9) and benzoyl chloride by the procedure described in Example 11. The title compound was recrystallized from 2-propanol/ether/petroleum ether. Mp 73°-77° C.

$k'$: 3.35.

Analysis: Calculated for $C_{26}H_{30}N_2O_4.1.5$ fumaric acid: C 63.15; H 5.96; N 4.60. Found: C 63.07; H 6.12; N 4.55.

EXAMPLE 17

O-3-Chlorobenzoyl Pilocarpic Acid Benzyl Ester. Salt with 1.5 equivalent fumaric acid.

(formula I; $R_1$=benzyloxy; $R_2$=3-chlorobenzoyl)

The compound was prepared from pilocarpic acid benzyl ester (see Example 3) and 3-chlorobenzoyl chloride by the procedure described in Example 11. The title compound was recrystallized from 2-propanol/ether/petroleum ether. Mp 77°-78.5° C.

$k'$: 4.08.

Analysis: Calculated for $C_{25}H_{27}ClN_2O_4.1.5$ fumaric acid: C 59.19; H 5.29; Cl 5.64; N 4.45. Found: C 59.04; H 5.43; Cl 5.52; N 4.41.

EXAMPLE 18

O-Butyryl Pilocarpic Acid 4-Methylbenzyl Ester. Salt with 1.5 equivalent fumaric acid.

(formula I; $R_1$=4-methylbenzyloxy; $R_2$=butyryl)

The compound was prepared form pilocarpic acid 4-methylbenzyl ester (see Example 5) and butyryl chloride by the procedure described in Example 11. The title compound was recrystallized from 2-propanol/ether/petroleum ether. Mp 89°-91° C.

k': 2.50.

Analysis: Calculated for $C_{23}H_{32}N_2O_4.1.5$ fumaric acid: C 60.62; H 6.67; N 4.87. Found: C 60.76; H 6.66; N 4.75.

EXAMPLE 19

O-Phenylacetyl Pilocarpic Acid Benzyl Ester. Salt with 1.5 equivalent fumaric acid.

(formula I; $R_1$=benzyloxy; $R_2$=phenylacetyl)

The compound was prepared from pilocarpic acid benzyl ester (see Example 3) and phenylacetyl chloride by the procedure described in Example 11. The title compound was recrystallized from 2-propanol/ether/petroleum ether. Mp 63°-65° C.

k': 2.15.

Analysis: Calculated for $C_{26}H_{30}N_2O_4.1.5$ fumaric acid: C 63.15; H 5.96; N 4.60. Found: C 62.99; H 6.12; N 4.36.

EXAMPLE 20

O-Nicotinoyl Pilocarpic Acid Benzyl Ester. Salt with 1.5 equivalent fumaric acid and 0.5 equivalent water.

(formula I; $R_1$=benzyloxy; $R_2$=nicotinoyl)

The compound was prepared from pilocarpic benzyl ester (see Example 3) and nicotinoyl chloride by the procedure described in Example 11. The title compound was recrystallized from 2-propanol/ether/petroleum ether. Mp. 71°-75° C.

k': 1.02.

Analysis: Calculated for $C_{24}H_{27}N_3O_4.1.5$ fumaric acid. 0.5 water: C 59.60; H 5.67; N 6.95. Found: C 59.75; H 5.92; N 6.79.

IN-VITRO RELEASE OF PILOCARPINE FROM PILOCARPIC ACID ESTERS

Solutions of various esters of pilocarpic acid (10 mg/ml) in various buffer solutions (pH 3.5-10) were kept at 37° C. and at various times analyzed by HPLC assays for intact esters (the same system as described above for the determination of the capacity factors) as well as for pilocarpine and isopilocarpine and the corresponding pilocarpic acids (Bundgaard & Honoré Hansen, 1982). Analysis of the solutions showed a complete conversion of the pilocarpic acid esters to pilocarpine in the pH range investigated. From theoretical reasons it could be expected that besides direct ring-closure to yield pilocarpine, the esters would undergo an epimerization followed by ring-closure to yield the inactive isopilocarpine, and also a hydrolysis to yield the inactive pilocarpic acid, but the specific HPLC assays revealed only the formation of pilocarpine in quantitative yields. The assays would allow a formation of isopilocarpine or isopilocarpic acid of 1% to be detected. The rate of ring-closure of the esters increased with increasing hydroxide ion activity, i.e. with increasing pH, c.f. FIG. 1, which shows the pH-rate profile for the 4-chlorobenzylester of pilocarpic acid at 37° C. The half-times of pilocarpine formation from various pilocarpic acid esters at physiological conditions of pH and temperature are given in Table 1. It can be seen that by appropriate variation of the alcohol portion of the esters it is possible to vary the rate of ring-closure and hence to control and modify the rate of pilocarpine production.

Figure 2:
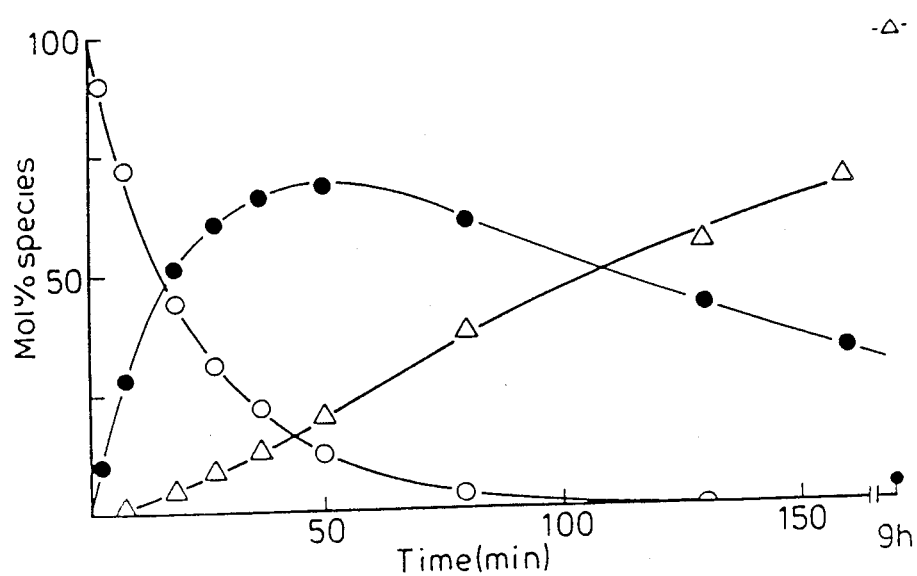
FIG. 2 shows time-courses for O-benzoyl pilocarpic acid 4-methylbenzyl ester (o), pilocarpic acid 4-methylbenzyl ester (●) and pilocarpine (Δ) during incubation of O-benzoyl pilocarpic acid 4-methylbenzyl ester in 75% human plasma (pH 7.4) at 37° C.

Using human plasma as a model of ocular tissue enzymes (a model based on studies by Hussain & Truelove (1976) and Anderson et al. (1980)) the two-step course of formation of pilocarpine was demonstrated with the compounds O-benzoyl pilocarpic acid 4-methylbenzyl ester and O-acetyl pilocarpic acid b 4-methylbenzyl ester prepared as described in Examples 11 and 12. When incubated in 75% human plasma (pH 7.4) at 37° C. these compounds degraded with half-lives of 16 and 24 minutes, respectively (Table 2), to yield pilocarpic acid 4-methylbenzyl ester in quantitative amounts as demonstrated using the HPLC assays referred to above. Following its formation this derivative cyclized quantitatively to pilocarpine with a half-time (83 minutes) almost identical to that observed in plasma-free buffer solutions (77 minutes). The time-courses for the various species in the experiment performed with the O-benzoyl derivative are shown in FIG. 2. At any time the sum of the concentrations of O-benzoyl pilocarpic acid 4-methylbenzyl ester, the intermediate pilocarpic acid 4-methylbenzyl ester and the final product pilocarpine is 100±3%. Half-lives in 75% human plasma of other di-esters are given in Table 3.

At similar reaction conditions, but without the presence of enzymes (plasma), the di-esters are very stable as can be seen from Table 2. It is of interest to note that the stability of these O-benzoyl derivatives is even greater than that of pilocarpine, pilocarpine having a shelf life of less than 1 year in aqueous solutions at pH 6.4 and 20° C. At pH greater than about 7 the hydrolysis of the compounds shows specific base catalysis with the catalytic rate contant $k_{OH}$ having values between 3 and 45 $M^{-1}$ $min^{-1}$ at 37° C. (Table 3). Thus, such pilocarpine prodrugs are characterized on the one hand by possessing a high in vitro stability, and on the other hand by being readily converted to pilocarpine in vivo.

These experiments show that the pilocarpic acid esters in fact are prodrug derivatives of pilocarpine in that the parent active compound is released at conditions similar to those prevailing in vivo.

THE LIPOPHILICITY OF THE PILOCARPINE PRODRUGS

The apparent partition coefficients (P) for some pilocarpic acid derivatives and pilocarpine were measured using the widely used 1-octanol/water system. A phosphate buffer of pH 7.4 was used as the aqueous phase. The values found for P and log P are listed in Tables 1 and 2, and values for log P are also listed in Table 3. The results show clearly that the pilocarpic acid derivatives are much more lipophilic than the parent drug. It is also obvious that by varying e.g. the alcohol portion of pilocarpic acid esters it is feasible to obtain prodrugs of pilocarpine with varying lipophilicity and hence to control and modify the corneal membrane permeability characteristics of the derivatives.

OTHER PHYSICOCHEMICAL PROPERTIES OF THE PILOCARPINE PRODRUGS

Due to their weak basic character (the $pK_a$ values being around 7.0) the compounds described in this application are readily soluble in aqueous solutions of pH 3-6 and may, like pilocarpine, form water-soluble salts with various acids. At such pH values the stability is much increased as compared with that at neutral and basic pH values. Thus, it was found that the shelf-life (i.e. times for 10% decomposition) of aqueous solutions of p-methylbenzyl pilocarpate of pH 4.0 was 3.8 years at 4° C. and about 1.5 years at 20° C. Compounds of the general formula I in which $R_2$ is different from hydrogen (e.g. benzoyl or acetyl) showed extremely high in vitro stabilities in weakly acidic solutions. Thus, the O-benzoyl pilocarpic acid benzyl ester was shown to possess maximum stability in aqueous solutions in the pH region 3-5. At these pH values solutions of the compound were predicted to have shelf-lives in excess of 8 years at 25° C. and 20 years at 20° C. as determined on the basis of temperature-accelerated kinetic stability studies.

TABLE 1

Partition coefficients (P) for various pilocarpic acid esters and half-times ($t_{0.5}$) of their cyclization to pilocarpine

| Ester | $t_{0.5}$ (min)[a] | P[b] | log P |
|---|---|---|---|
| 4-Chlorobenzyl | 30 | 347 | 2.54 |
| Benzyl | 50 | 66 | 1.82 |
| 4-Methylbenzyl | 77 | 204 | 2.31 |
| 4-tert.Butylbenzyl | 87 | 3310 | 3.52 |
| 2-Methylbenzyl | 139 | 186 | 2.27 |
| 2-Phenylethyl | 227 | 145 | 2.16 |
| Butyl | 820 | 38 | 1.58 |
| 1-(Phenyl)ethyl | 475 | 120 | 2.08 |
| Pilocarpine | | 0.7 | −0.15 |

[a]At pH 7.40 and 37° C.
[b]Between octanol and 0.05 M phosphate buffer solution pH 7.40.

TABLE 2

Partition coefficients (P) for O—acyl derivatives of pilocarpic acid 4-methylbenzyl ester and half-times ($t_{0.5}$) of their hydrolysis to pilocarpic acid 4-methylbenzyl ester at 37° C.

| | | | $t_{0.5}$ | |
|---|---|---|---|---|
| Ester | P[a] | log P | pH 7.4 buffer | 75% human plasma[b] |
| O—Benzoyl | 50100 | 4.70 | 4800 h[c] | 16 min |
| O—Acetyl | 1450 | 3.16 | 1500 h[c] | 24 min |

[a]Between octanol and 0.05 M phosphate buffer solution pH 7.40.
[b]In 75% human plasma (pH 7.4) the 4-methylbenzyl ester of pilocarpic acid and subsequently pilocarpine are formed in 100% yield from the O—acyl esters as determined by HPLC.
[c]The hydrolysis is specific base-catalyzed and the data shown were obtained by extrapolating experimental rate constants at pH 10-12 to pH 7.4. At 20° C. the $t_{0.5}$ values were 4.5 and 1.4 years, respectively.

TABLE 3

Rate data (at 37° C.) and lipophilicity of pilocarpic acid di-esters

| $R_1$ | $R_2$ | $t_{0.5}$ (min) human plasma (75%) | $k_{OH}$* ($M^{-1}$ $min^{-1}$) | log P octanol/ buffer pH 7.4 |
|---|---|---|---|---|
| Benzyloxy | benzoyl | 12 | 3.8 | 4.22 |
| 4-Chlorobenzyloxy | benzoyl | 17 | 3.4 | 4.75 |
| 2-Phenylethyloxy | benzoyl | 15 | 3.8 | 4.60 |
| 4-Methylbenzyloxy | benzoyl | 16 | 4.0 | 4.70 |
| 4-Methylbenzyloxy | acetyl | 24 | 12.6 | 3.16 |
| 4-Methylbenzyloxy | butyryl | 15 | 3.5 | 4.09 |
| Benzyloxy | phenylacetyl | 4 | 21.7 | 3.85 |
| Benzyloxy | 3-chlorobenzoyl | 25 | 14.6 | 4.93 |
| Benzyloxy | nicotinoyl | 6 | 44.4 | 2.90 |

*Based on hydroxide on activity

OPHTHALMIC PUPILLARY DIAMETER OR MIOSIS STUDY

Figure 3:
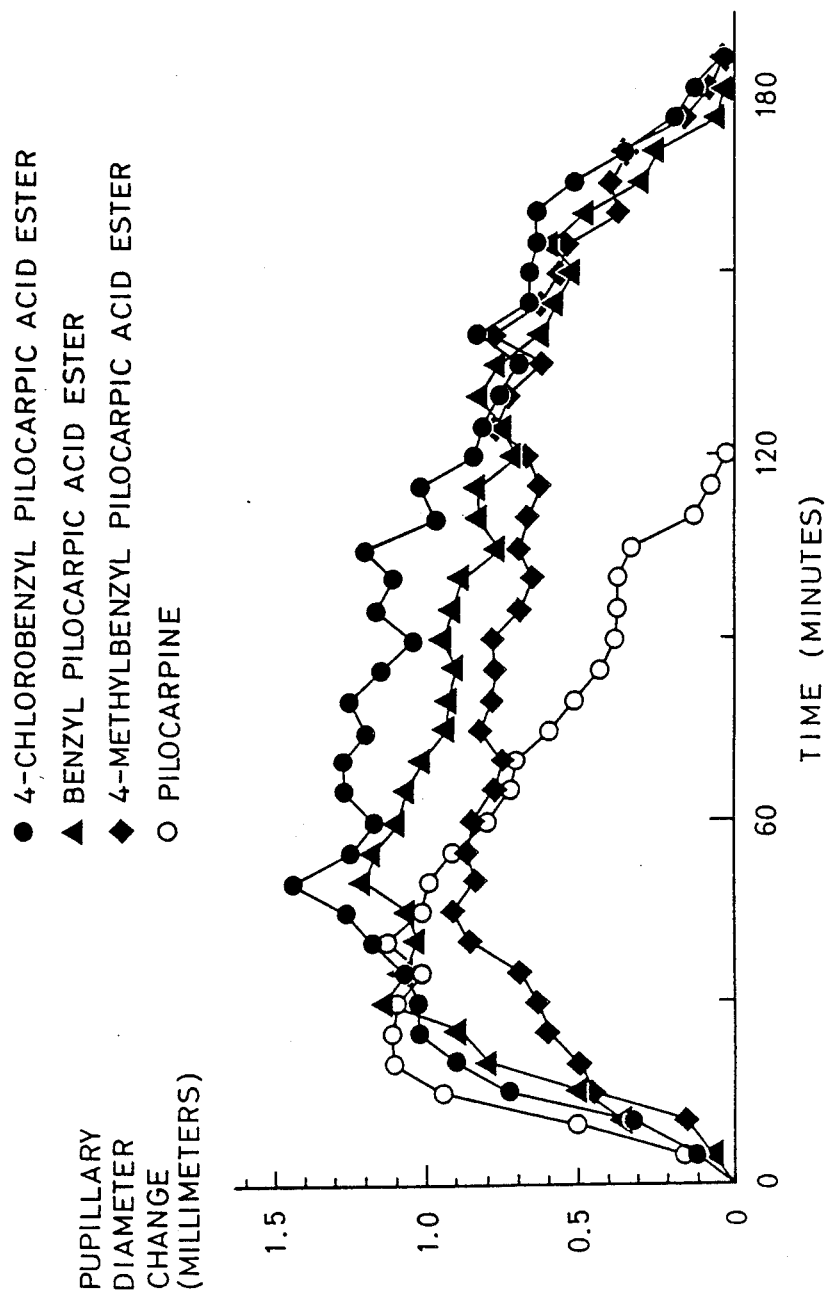
FIG. 3 shows miosis-time profiles, i.e. plots of the average observed changes in pupillary diameter as a function of time, following the instillation of 25.0 μl of the pH-adjusted, isotonic solutions in equimolar concentrations (0.5% pilocarpine nitrate equivalent) of the compounds indicated.
Figure 4:
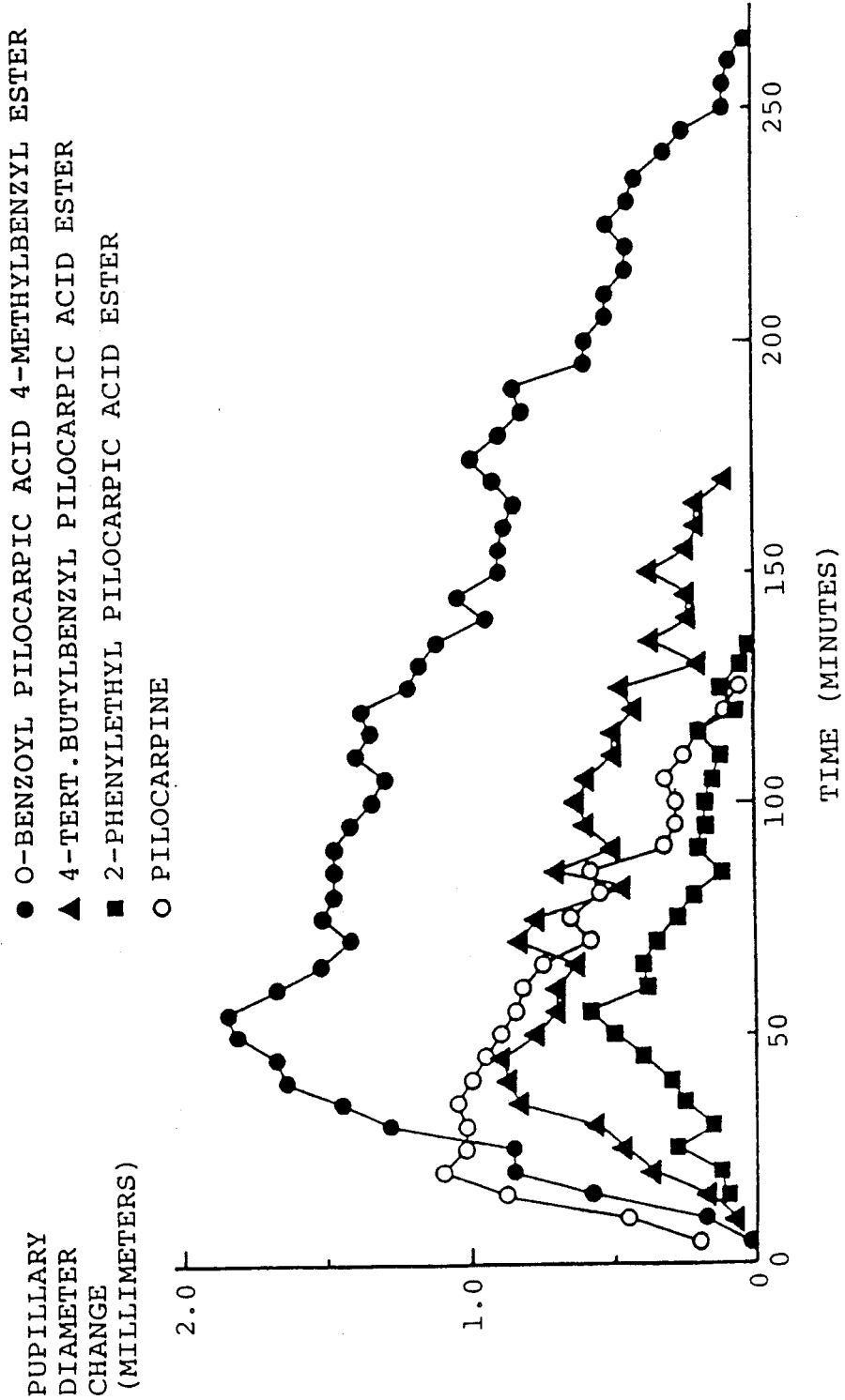
FIG. 4 shows miosis-time profiles following the instillation of 25.0 μl of the pH-adjusted, isotonic solutions in equimolar concentrations (0.5% pilocarpine nitrate equivalent) of the compounds indicated.

Solutions of equivalent molar concentrations (0.5% pilocarpine nitrate equivalent) with respect to content of pilocarpine base were prepared of benzyl pilocarpate (0.58% w/v), 4-chlorobenzyl pilocarpate (0.65% w/v), 4-methylbenzyl pilocarpate (0.61% w/v), and pilocarpine (0.38% w/v), the solutions being made isotonic with sodium chloride and the pH adjusted to 4.5 with hydrochloric acid. Twenty-five microliter volumes of each solution were administered by topical ophthalmic instillation to male albino rabbits, and pupillary diameter changes or miotic activities in the eyes of the rabbits were recorded as a function of time, and were compared. A detailed description of the procedure for the miosis study is given in Mitra & Mikkelson (1982) and references cited therein. The results of the cross-over studies are graphically presented in FIG. 3. It is evident from the figure that the esters of pilocarpic acid are prodrugs of pilocarpine, that release pilocarpine and result in pilocarpine activity. However, the effects resulting from application of the derivatives, as compared to pilocarpine, per se, are significantly greater in their overall effect and most significantly and dramatically longer with respect to the duration of their effect. Compounds of the general formula I, in which $R_2$ is different from hydrogen (e.g. benzoyl) showed even greater and more prolonged activity. Thus, the miotic activity observed after administration of a solution of O-benzoyl pilocarpic acid 4-methylbenzyl ester lasted for 4.5 hours as shown in FIG. 4. The equivalent concentrations and pH were the same as in the above experiment. As seen from the figure the bioavailability of this latter compound is approximately 4-fold greater than that of pilocarpine. FIG. 4 also shows the miotic activity of 4-tert.butyl benzyl pilocarpic acid ester and 2-phenylethyl pilocarpic acid ester.

Figure 5:
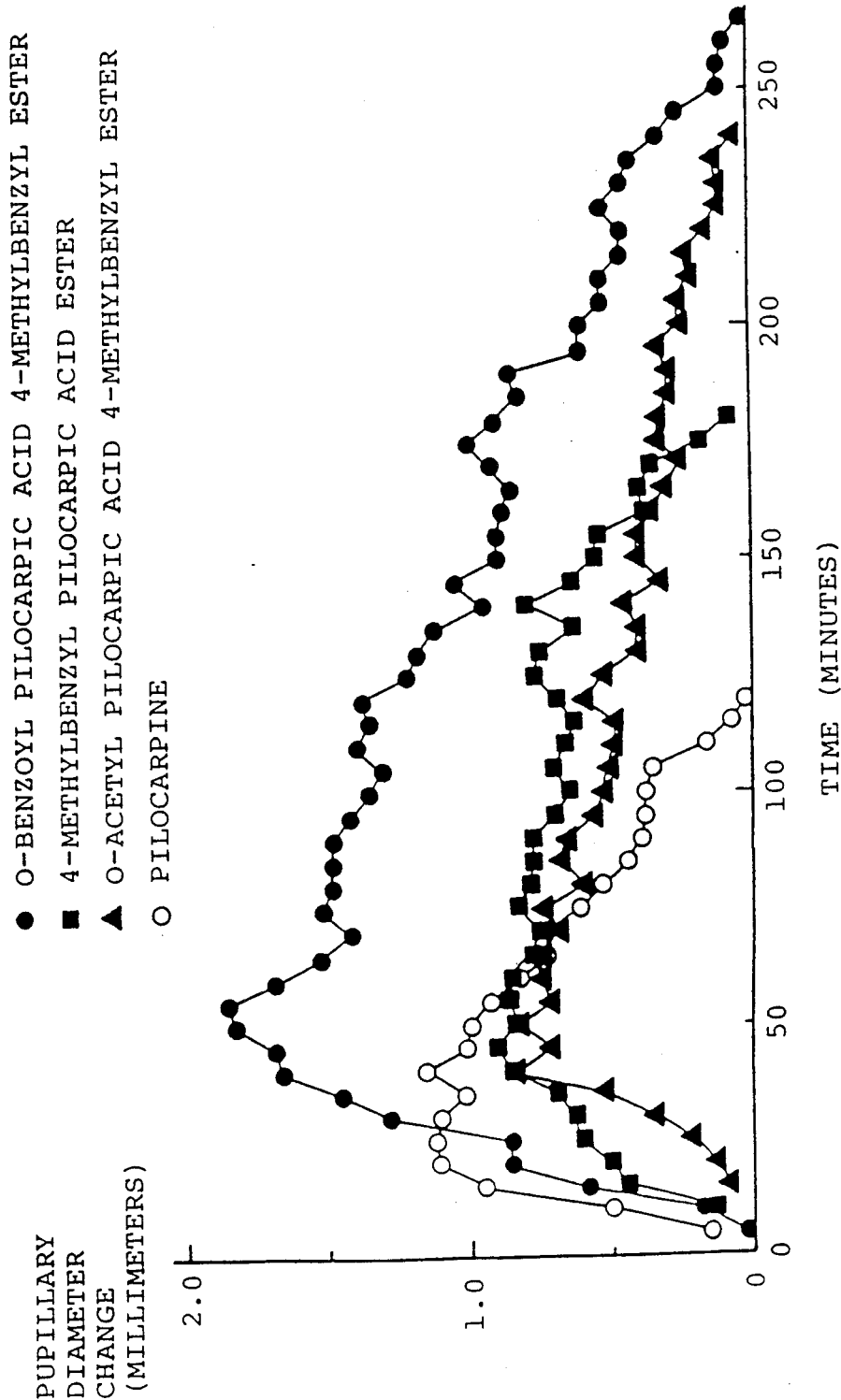
FIG. 5 shows miosis-time profiles following the instillation of 25.0 μl of the pH-adjusted, isotonic solutions in equimolar concentrations (0.5% pilocarpine nitrate equivalent) of the compounds indicated.

In FIG. 5 is demonstrated the comparative activities of two di-esters and one mono-ester in comparison to pilocarpine. The compounds are: 4-methylbenzyl pilocarpic acid ester, O-benzoyl pilocarpic acid 4-methylbenzyl ester, and O-acetyl pilocarpic acid 4-methylbenzyl ester. In each of these three derivatives the $R_1$-substituent is the 4-methylbenzyloxy group. These data also demonstrate the extended duration of the miotic response. Duration of the activity of the di-esters is seen to be approximately 4.5 hours.

Figure 6:
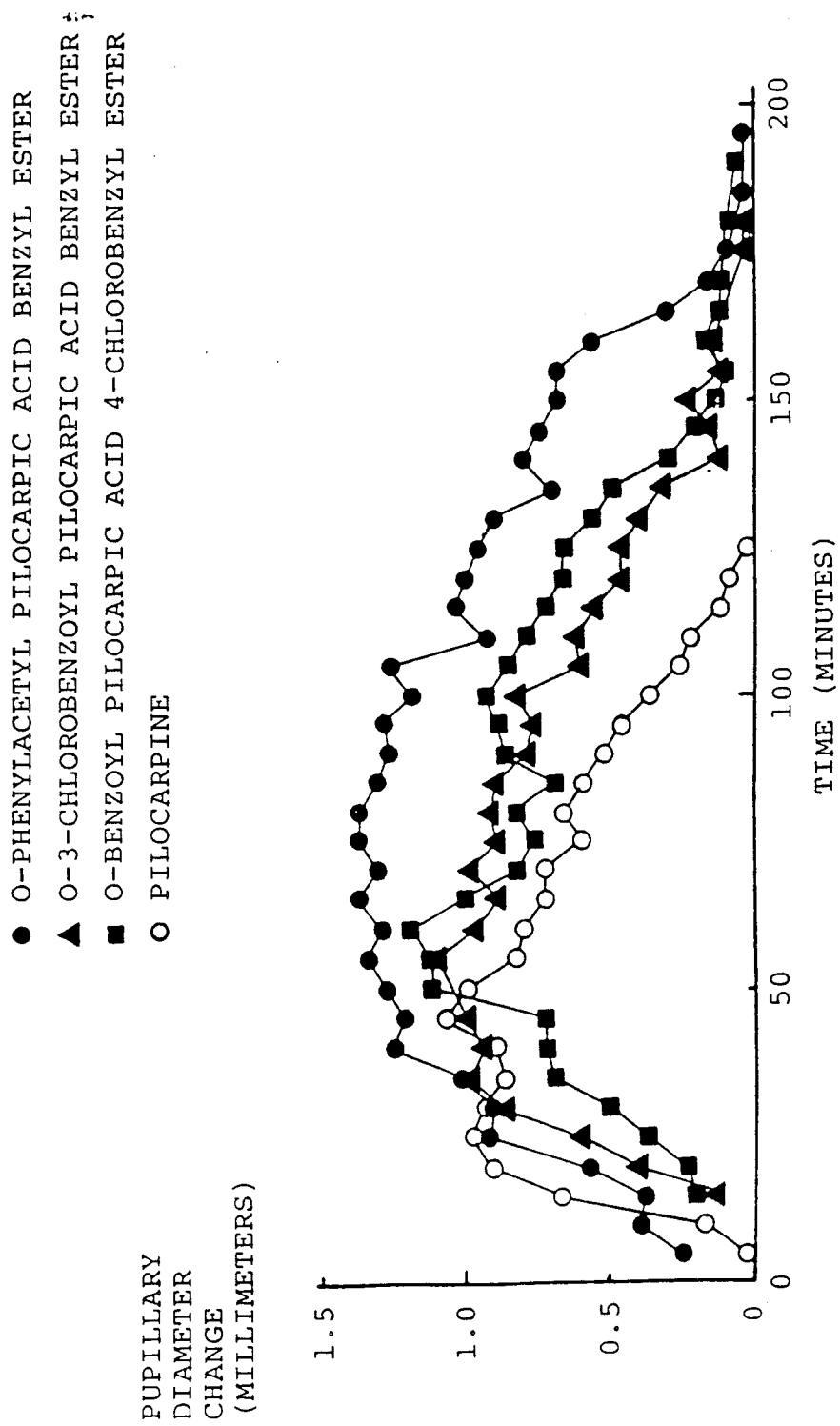
FIG. 6 shows miosis-time profiles following the instillation of 25.0 μl of the pH-adjusted, isotonic solutions of the compounds indicated. The concentrations of the solutions of O-phenylacetyl pilocarpic acid benzyl ester, O-3-chlorobenzyl pilocarpic acid benzyl ester, and pilocarpine corresponded to 0.25% (pilocarpine nitrate equivalent). The concentration of the solution of O-benzoyl pilocarpic acid 4-chlorobenzyl ester corresponded to 0.125% (pilocarpine nitrate equivalent).

FIGS. 6 and 7 show the activities of further di-ester derivatives in comparison with pilocarpine. In FIG. 6 the compounds are the O-benzoyl 4-chlorobenzyl, the O-phenylacetyl benzyl, and the O-3-chlorobenzoyl benzyl pilocarpic acid esters. In FIG. 7 the compounds are the O-benzoyl benzyl, the O-butyryl 4-methylbenzyl and the O-nicotionyl benzyl pilocarpic acid esters. All compounds were administered in equivalent molar doses of 25 μl of 0.25% (pilocarpine nitrate equivalent) solutions, except for the O-benzoyl 4-chlorobenzyl ester where the concentration used was 0.125% (pilocarpine nitrate equivalent). Again, the extended duration is apparent. Thus, even though the dosage level is less than in the previous experiments, the miotic effect is apparent for up to 4.5 hours after administration.

REFERENCES CITED

Anderson, J. A., W. L. Davis & C.-P. Wei: Invest. Ophthalmol. Vis. Sci. 19, 817 (1980)
Bodor, N. S.: U.S. Pat. No. 4,061,722 (1977)
Bundgaard, H. & S. Honoré Hansen: Int. J. Pharm. 9, 281 (1982)
Hussain, A. & J. E. Truelove: J. Pharm. Sci. 65, 1510 (1976)
Justin, M., A. Urtti & L. Salminen: Acta Pharm. Fenn. 90, 289 (1981)
Koda, R. T., F. J. Dea, K. Fung, C. Elison & J. A. Biles: J. Pharm. Sci. 62, 2021 (1973)

Lee, V. H.-L. & J. R. Robinson: J. Pharm. Sci. 68, 673 (1979)
Lerman, S. & B. Reininger: Can. J. Ophthalmol. 6, 14 (1971)
Mitra, A. K. & T. J. Mikkelson: Int. J. Pharm. 10, 219 (1982)
Norell, S. E.: Pharmacy Int. 3, 123 (1982)
Norell, S. E. & P.-A. Granström: Br. J. Ophthalmol. 64, 137 (1980)
Patton, T. F. & M. Francoeur: Am. J. Ophthalmol. 85, 225 (1978)
"Remington's Pharmaceutical Sciences", Sixteenth Edition (1980) Mack Publishing Company, Easton
Robinson, J. R. (ed.): "Ophthalmic Drug Delivery Systems", American Pharmaceutical Association, Washington, D.C. (1980)
Shell, J. W. & R. W. Baker: Ann. Ophthalmol. 6, 1037 (1974)

What is claimed is:

1. Compounds of the formula I

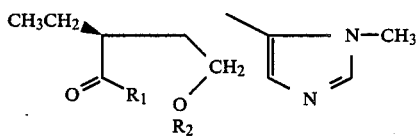

wherein
(a) $R_1$ is a group of the formula II

wherein
$R_3$ is $C_{1-8}$ alkyl; phenyl; phenyl substituted with up to three halogen, $C_{1-4}$ alkyl, hydroxy, $C_{1-4}$ alkoxy, or phenoxy groups; phenyl-$C_{1-4}$ alkyl wherein the phenyl group may be substituted with up to three halogen, $C_{1-4}$ alkyl, hydroxy, $C_{1-4}$ alkoxy, or phenoxy groups; and phenyl-$C_{2-5}$-monounsaturated alkenyl wherein the phenyl group may be substituted with up to three halogen, $C_{1-4}$ alkyl, hydroxy, $C_{1-4}$ alkoxy or phenoxy groups; or
(b) $R_1$ is a group of the formula III

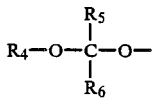

wherein
$R_4$, $R_5$ and $R_6$ may each have the same meaning as $R_3$, or $R_5$ and $R_6$ may each represent hydrogen; or
$R_4$ is a group of the formula IV

wherein
$R_7$ has the same meaning as $R_3$ or is selected from the group consisting of pyridinyl, thienyl, thiazolyl, oxazolyl, imidazolyl, isoxazolyl, isothiazolyl, furanyl, pyrimidinyl, oxazinyl or thiazinyl; or
(c) $R_1$ is a group of the formula V

wherein
$R_8$ is polyhalogenated $C_{1-4}$ alkyl or a group of the formula VI

wherein
$R_3$ is defined above and
(d) $R_2$ is hydrogen or a group of either of formulas IV or VI; and pharmaceutically acceptable acid addition salts thereof.

2. Compounds according to claim 1, wherein $R_2$ is a group of either of the formulas IV or VI.

3. Compounds according to claim 1, wherein $R_2$ is a group of the formula IV.

4. Compounds according to claim 1, wherein $R_1$ is a group of the formula II and $R_3$ is phenyl-$C_{1-4}$ alkyl or substituted phenyl-$C_{1-4}$ alkyl wherein the phenyl group may be substituted with up to three halogen, $C_{1-4}$ alkyl, hydroxy, $C_{1-4}$ alkoxy, or phenoxy groups.

5. Compounds according to claim 4, wherein $R_2$ is a group of either of formulas IV or VI.

6. Compounds according to claim 5, wherein $R_2$ is a group of the formula IV.

7. Compounds according to claim 6, wherein $R_7$ is $C_{1-8}$ alkyl; phenyl; phenyl substituted with up to three halogen, $C_{1-4}$ alkyl, hydroxy, $C_{1-4}$ alkoxy, or phenoxy; 3-pyridyl or 4-pyridyl.

8. Compounds according to claim 7, wherein $R_2$ is acetyl or benzoyl.

9. Compounds according to claim 4, wherein
$R_1$ is benzyloxy, 2-phenylethyloxy, 4-chlorobenzyloxy, 4-methylbenzyloxy, or 4-tert.butylbenzyloxy, and
$R_2$ is hydrogen, acetyl, propionyl, butyryl, or benzoyl.

10. Compounds according to claim 9, wherein
$R_1$ is benzyloxy, 4-methylbenzyloxy, or 4-chlorobenzyloxy, and
$R_2$ is acetyl, propionyl, butyryl or benzoyl.

11. A compound according to claim 1, selected from the group consisting of:
O-benzoyl pilocarpic acid 4-methylbenzyl ester,
O-benzoyl pilocarpic acid benzyl ester,
O-benzoyl pilocarpic acid 4-chlorobenzyl ester,
O-butyryl pilocarpic acid 4-methylbenzyl ester,
O-phenylacetyl pilocarpic acid benzyl ester,
O-acetyl pilocarpic acid 4-methylbenzyl ester,
O-butyryl pilocarpic acid benzyl ester, and
O-propionyl pilocarpic acid benzyl ester,
and pharmaceutically acceptable acid addition salts thereof.

12. A compound according to claim 11, viz. O-benzoyl pilocarpic acid benzyl ester, and pharmaceutically acceptable acid addition salts thereof.

13. A pharmaceutical composition for topical use in the treatment of glaucoma, comprising an antiglaucoma effective amount of a compound according to claim 1 in a pharmaceutically acceptable, inert ophthalmic carrier.

14. A method for treating glaucoma, comprising ophthalmic administration to warm-blooded animals in need of treatment for glaucoma of an anti-glaucoma effective amount, in the range of about 0.005 mg to 4 mg per dose, of a compound according to claim 1.

* * * * *

UNITED STATES PATENT AND TRADEMARK OFFICE
CERTIFICATE OF CORRECTION

PATENT NO. : 4,742,073

DATED : May 3, 1988

INVENTOR(S) : Bundgaard et al.

It is certified that error appears in the above-identified patent and that said Letters Patent is hereby corrected as shown below:

In the ABSTRACT, and in Columns 2 and 27, general formula I should show the bond between the left hand part of the molecule and the methylene group (represented as an oblique line) attached to the right hand imidazole moiety; the formula should thus appear as follows:

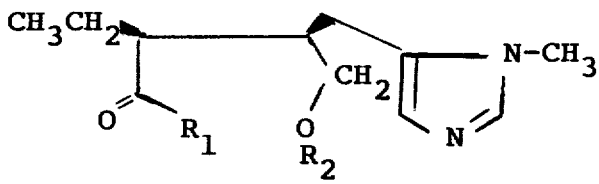

Column 2, line 19, "therapeutic" should read --therapeutic activity--.

Column 5, line 46, "CI" should read --Cl--.

Column 20, line 55, "he sodium salt" should read --the sodium salt--.

UNITED STATES PATENT AND TRADEMARK OFFICE
CERTIFICATE OF CORRECTION

PATENT NO. : 4,742,073

DATED : May 3, 1988

INVENTOR(S) : Bundgaard, et al.

It is certified that error appears in the above-identified patent and that said Letters Patent is hereby corrected as shown below:

Column 22, line 21, "form" should read --from--; and
          line 64, "form" should read --from--.

Column 25, line 57, the footnote below Table 3, "on hydroxide on activity" should read --on hydroxide ion activity--.

Signed and Sealed this

Fourth Day of April, 1989

Attest:

DONALD J. QUIGG

Attesting Officer

Commissioner of Patents and Trademarks